United States Patent [19]

Lavender

[11] Patent Number: 4,898,675
[45] Date of Patent: Feb. 6, 1990

[54] SYSTEM AND METHOD FOR CONTINUOUSLY FRACTIONATING BLOOD IN SITU

[76] Inventor: Ardis R. Lavender, 15 Deerfield Rd., Chappaqua, N.Y. 10514

[21] Appl. No.: 809,923

[22] Filed: Dec. 16, 1985

Related U.S. Application Data

[63] Continuation-in-part of Ser. No. 523,007, Aug. 15, 1983.

[51] Int. Cl.⁴ .................................................. B01D 13/00
[52] U.S. Cl. ...................................... 210/651; 210/90; 210/321.65; 210/321.75
[58] Field of Search .................. 210/927, 321.1, 433.2, 210/321.2, 321.3, 87, 651, 90, 434, 101, 456, 321.65, 321.75

[56] References Cited

U.S. PATENT DOCUMENTS

| | | | |
|---|---|---|---|
| 4,464,172 | 8/1984 | Lichtenstein | 128/DIG. 13 X |
| 4,469,593 | 9/1984 | Ishihara et al. | 210/321.1 X |
| 4,582,598 | 4/1986 | Bilstad et al. | 210/927 X |
| 4,657,529 | 4/1987 | Prince et al. | 604/6 |
| 4,668,400 | 5/1987 | Veech | 210/96.2 X |
| 4,729,829 | 3/1988 | Duggins | 210/321.8 X |

Primary Examiner—Frank Spear
Attorney, Agent, or Firm—Emrich & Dithmar

[57] ABSTRACT

A system, method and device for continuously fractionating blood in situ. The fractionating device is connected in a closed loop to the donor and includes interleaved blood plates and blood fraction plates separated by a semipermeable membrane. Grooves in the plates direct blood flow and blood fraction collection. Uniform distribution among the plates and intraplate is obtained by manifolds.

The input and output pressures of the blood pump are sensed and inputed to an microprocessor, into which donor data including weight, sex, and hematocrit is also keyed by the user. The microprocessor operates under program control to calculate, based on the donor data, the amount of plasma to be collected and the amount of anticoagulant to be added. The program controls the operation of the extracorporeal devices, regulates the operating parameters, and stops the procedure when the predetermined amount of plasma has been obtained.

48 Claims, 12 Drawing Sheets

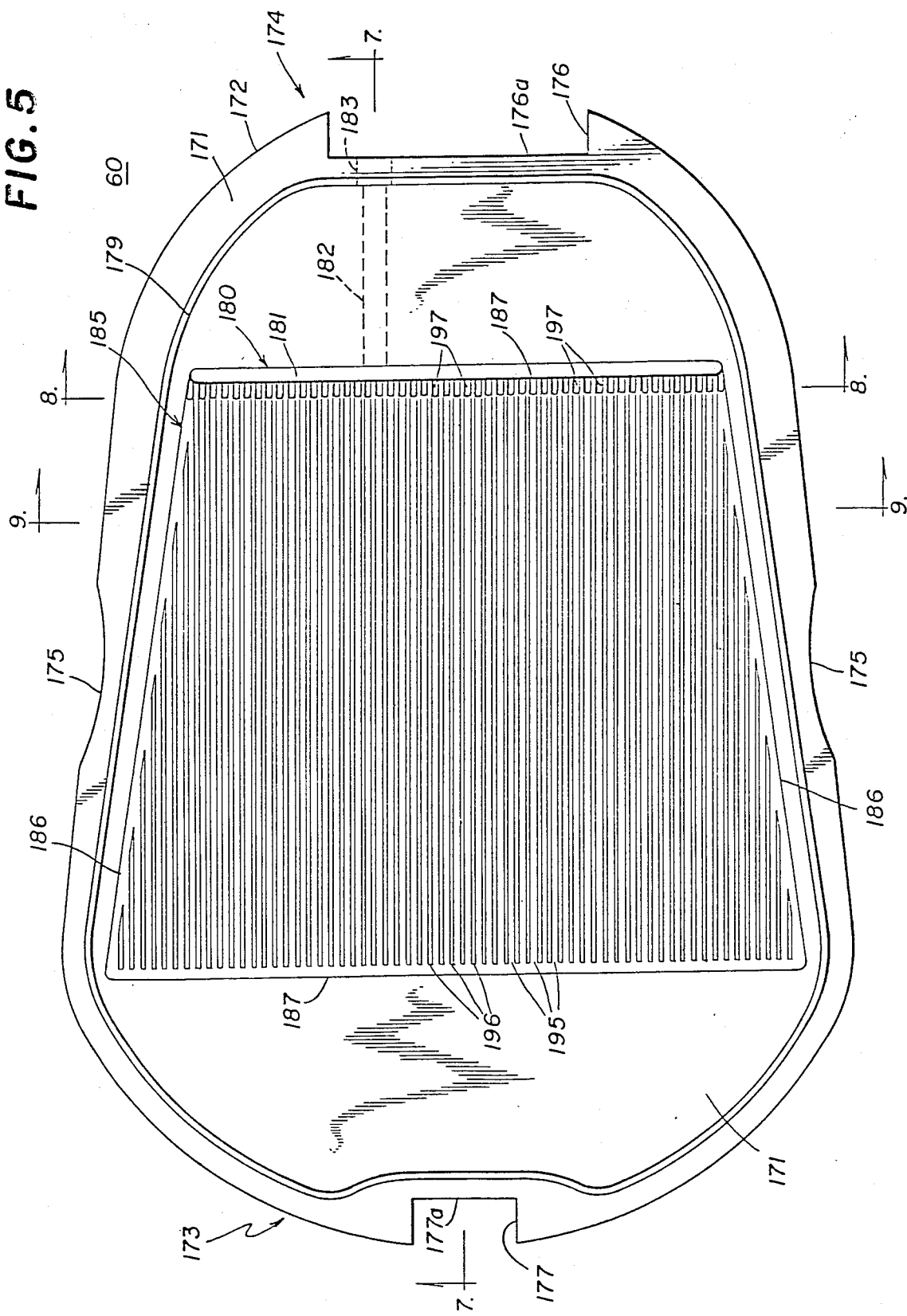

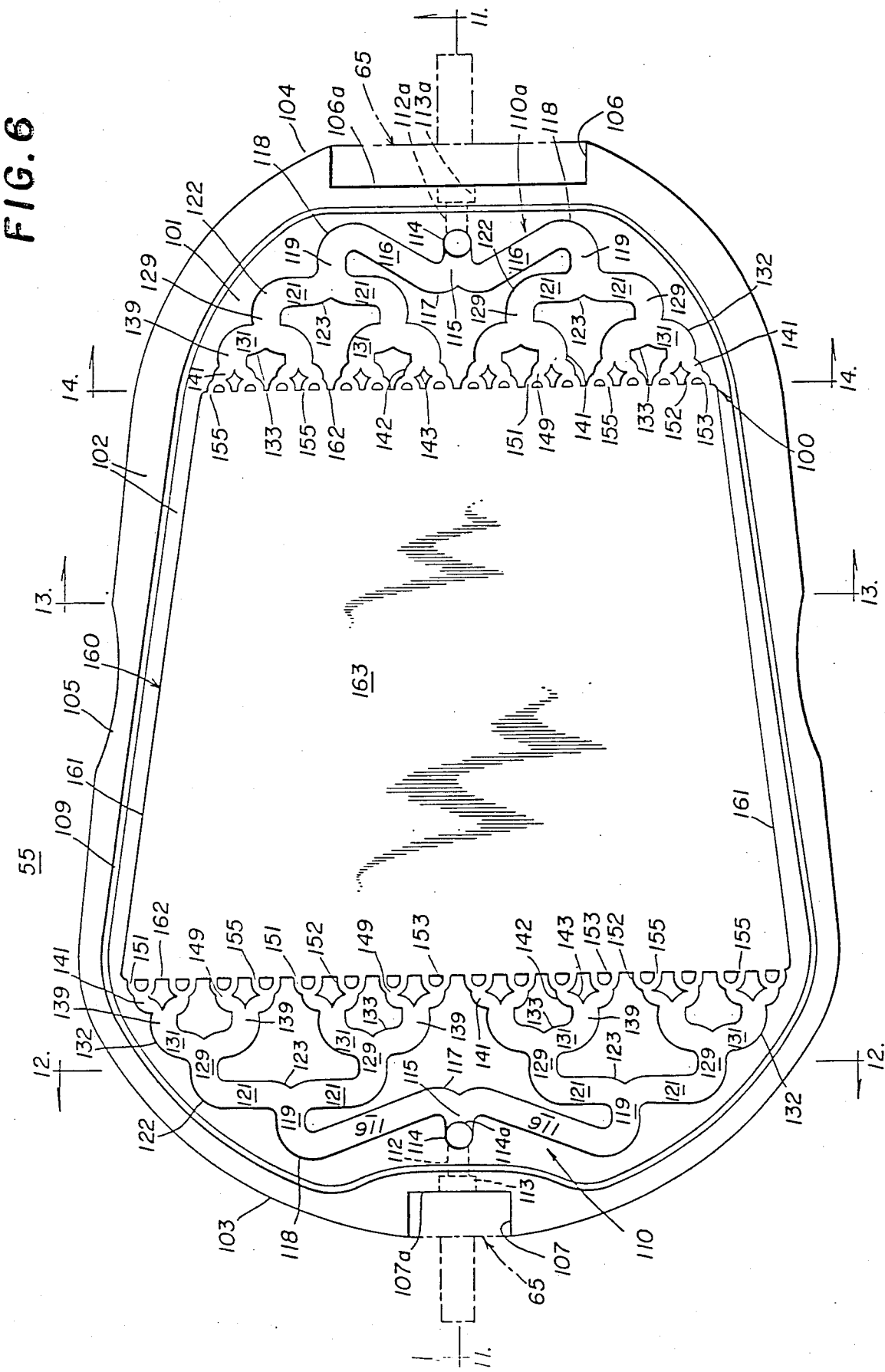

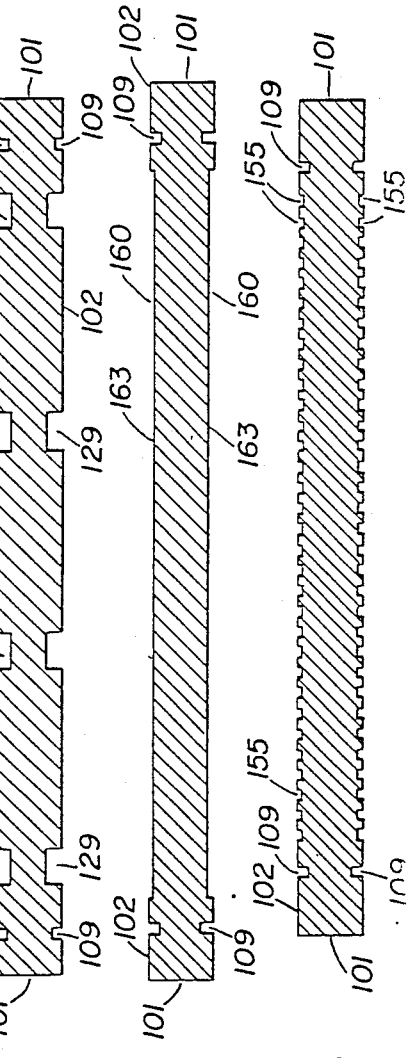

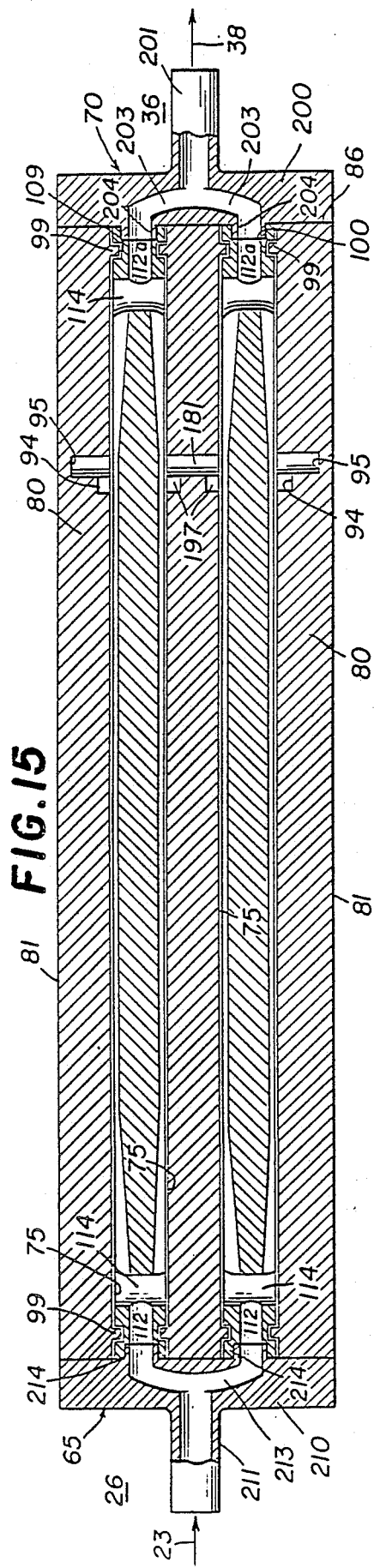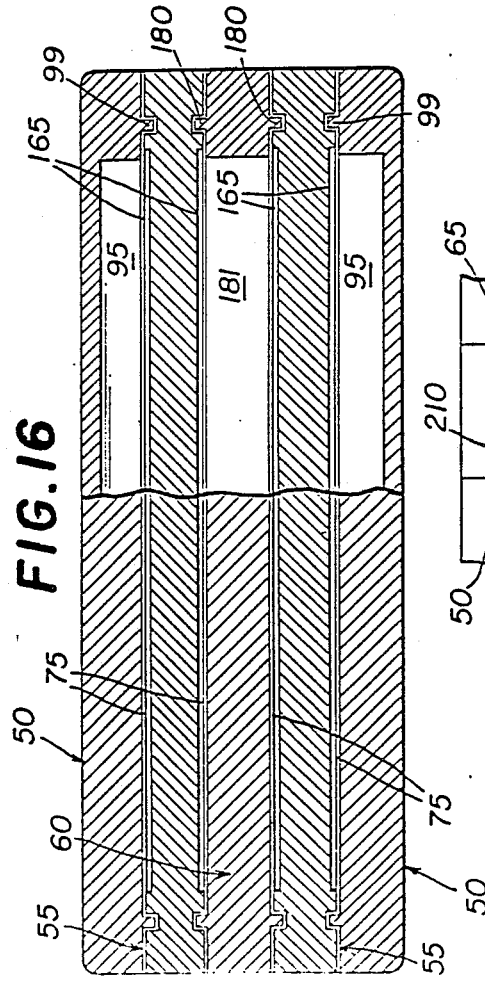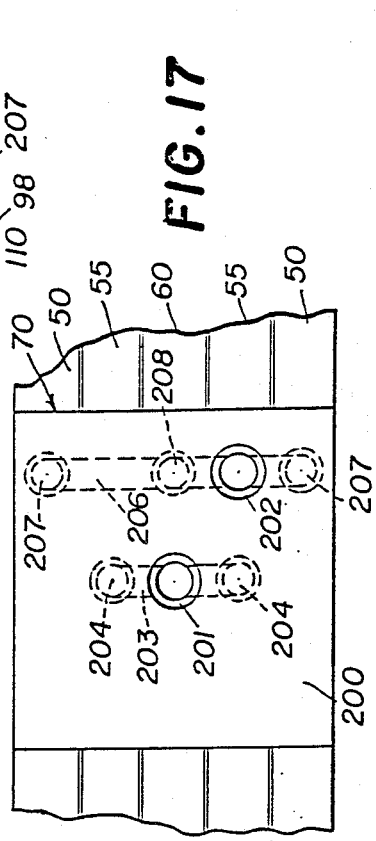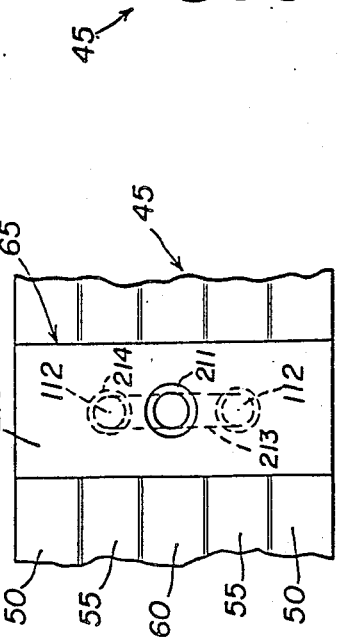

SYSTEM AND METHOD FOR CONTINUOUSLY FRACTIONATING BLOOD IN SITU

CROSS REFERENCE TO RELATED APPLICATION

This is a continuation-in-part of copending application Ser. No. 523,007, filed Aug. 15, 1983.

BACKGROUND OF THE INVENTION

The present invention relates to the collection of blood, and in particular, to the fractionating of blood to collect blood substances, such as plasma, cells, or some specific constituent of blood. There are many reasons for fractionating blood to separate various components thereof, one of the most important being to obtain plasma. Plasma has been found to be efficacious in the treatment of various disease states and is generally useful since it may be stored for long periods in comparison to whole blood which has a rather short shelf life.

When harvesting plasma from a donor, it is preferred to return the formed elements of the blood, including red blood cells, white blood cells and platelets, to the donor so that frequent plasma harvestings may be effected. Traditionally, plasma is harvested by transferring blood from a donor into a blood bag containing a fixed amount of anticoagulant solution and thereafter centrifuging the blood to separate the plasma from the formed elements of the blood. The formed elements are thereafter reconstituted with a saline solution and reintroduced to the donor. For a variety of reasons, generally each donor must undergo two such operations for each plasma donation.

The traditional manner of harvesting plasma involves several risks and discomforts to the donor. A principal risk is the chance that the reconstituted blood returned to the donor will not be the donor's, a situation which may result in fatalities. Other attendant risks are those of infection and the like. The discomfort involves, among other things, the inordinate length of time required to permit two samples of blood to be taken with the required centrifuging of each sample, the large volume of blood removed for processing, the reconstituting of the formed elements into a saline solution and reintroducing same to the donor. It is clear that a simpler, safer, speedier system for harvesting plasma is needed and has been needed for a considerable length of time.

One such proposed alternative to the above-described traditional method of harvesting plasma is described in the Blatt et al. U.S. Pat. No. 3,705,100 issued Dec. 5, 1972, which patent discloses an apparatus and method for harvesting plasma from whole blood which includes a cylinder having a reservoir and on the bottom of the cylinder a spiral flow path formed by a spiral groove which sits on top of a membrane having a predetermined pore size. Blood in the reservoir is forced through the spiral path by means of a pressurized gas driving fluid. A second embodiment of the apparatus is disclosed in which a hypodermic syringe is used to withdraw blood from a patient and thereafter introduce the blood into the same sort of spiral flow path as previously described.

The Blatt et al. apparatus and process is not utilized for the commercial production of plasma. The Blatt et al. process and method is, like the described prior art, a batch process and requires withdrawing blood from a donor, treating it and thereafter reintroducing the blood into the donor with all the attendant risks and time delays previously described. Accordingly, none of the serious drawbacks of the prior art have been solved by the Blatt et al. disclosure.

Another disadvantage of existing plasma harvesting techniques is that neither the amount of plasma collected nor the amount of anticoagulant added thereto is tailored to the individual donor. It is known that the total circulating plasma volume and plasma concentration in a human donor vary as a functions of body weight and hematocrit (red blood cell concentration). In general, the plasma volume varies directly with body weight. For example, plasma volume averages approximately 0.05 liters per kilogram of body weight or about 22.7 ml. per pound of body weight. Thus, plasma volume in a 150 lb. man is approximately 3.4 liters. Plasma concentration varies inversely with hematocrit. Thus, e.g., in a one liter donation with a hematocrit of 45%, the plasma concentration will be 55% or 550 ml.

Body weight of most donors may vary from 110 to 300 lbs., and it has been found that hematocrit varies from about 38% to about 54%. It would be impractical and prohibitively expensive to have different size blood bags and different amounts of anticoagulant to accommodate all the possible variations of body weight and hematocrit values in donors. Consequently, current government guidelines specify two classes of donors, viz., those having a body weight of 174 lbs. or less and those having a body weight over 174 lbs. Current regulations also specify a maximum volume of blood, not plasma, which can be extracted per donor episode. The maximum blood volume is 1 liter per session in a donor of 174 lbs. or less and 1200 ml. per session in a donor of greater than 174 lbs. Since hematocrit varies from 38% to 54%, plasma harvested will vary from 460 to 620 mls. in a 1 liter donation. Therefore, it can be seen that, under current government guidelines, the volume of plasma harvested in a single donor episode as a percent of the total circulating plasma in the donor can vary over a fairly wide range.

Taking the example of a 150 lb. man, having about 3.4 liters of circulating plasma, a one liter whole blood donation may represent anywhere from 13.5% to 18.2% of the donor's initial circulating plasma, depending upon the donor's hematocrit value. It is generally accepted that the maximum percentage of total circulating plasma which safely can be donated in a single episode is 18%. Data collected from actual plasmapheresis at a number of donor centers indicate that the percent of total circulating plasma volume removed ranged from 10% to 22.8% and the percent of total circulating blood volume removed ranged from 4.7% to 14.1%, with small donors giving disproportionately larger amounts of plasma than large donors. Therefore, it is apparent that under current procedures, the plasma harvested from many large donors is considerably less than the maximum safe amount, and that harvested from many small donors is in excess of the maximum safe amount.

Additionally, under current government regulations, one unit of anticoagulant is added to every ten units of collected whole blood. Typically, the anticoagulant is added to the blood bag before collection of the blood. Thus, for example, a blood bag for collecting 500 mls. of whole blood from a person 174 lbs. or less would contain 50 ml. of anticoagulant, while a blood bag for collecting 600 ml. of whole blood from a donor over 174 lbs. would contain 60 ml. of anticoagulant.

But blood coagulation factors are present only in plasma. Because the plasma volume of whole blood varies with hematocrit, basing anticoagulant volume on the whole blood volume is, of necessity, inaccurate. Blood from donors with low hematocrits may receive too little anticoagulant and blood from donors with high hematocrits may receive too much. When the amount is too little, blood may clot. When it is too much, systemic toxicity secondary to calcium depletion may occur.

SUMMARY OF THE INVENTION

It is a general object of the present invention to provide an apparatus and method for separating a blood substance from a source of blood which avoids the disadvantages of prior methods and apparatuses while affording additional structural and operating advantages.

An important feature of the invention is the provision of a method of collecting blood or blood products as a function of some physiologic constant.

Another feature of the invention is the provision of a method of separating a blood substance from a source of blood based on the initial amount of the substance in the blood source.

Still another important feature of the invention is the provision of a method for accurately, safely and economically collecting plasma from a source of blood.

In connection with the foregoing feature, it is another feature of the invention to provide a method for harvesting blood plasma from a human donor as a function of circulating plasma volume in the donor.

It is another feature of the invention to provide a method for accurately harvesting the maximum safe amount of plasma from a donor.

Still another feature of the invention is the provision of a method for dilution of a blood substance as a function of the amount of the substance in the blood source.

In connection with the foregoing feature, yet another feature of the invention is the provision of a method of adding anticoagulant to a source of blood as a function of plasma concentration in the blood.

In connection with the foregoing features, another feature of the invention is the provision of a system for performing these methods.

Another feature of the invention is the provision of methods and systems of the type set forth in which the blood substance is separated and diluent is added thereto continuously and automatically.

Certain of these features are attained by providing a method of separating a blood substance from a source of blood, comprising: ascertaining the initial amount of the substance in the blood source, and separating the substance from the blood source until a predetermined percentage of the initial amount of the substance has been separated.

Other features are attained by providing a method of diluting a blood substance in a source of blood, comprising: ascertaining the initial amount of the substance in the blood source, and adding a diluent to the blood in an amount equal to a predetermined percentage of the initial amount of the substance in the blood source.

Still other features of the invention are attained by providing a system for collecting plasma from a source of blood, comprising means for ascertaining the volume of plasma in the source of blood, and means for separating a predetermined portion of the plasma from the source of blood.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 5 is an enlarged plan view of an internal blood fraction collection plate;

FIG. 6 is an enlarged plan view of a blood plate;

FIG. 7 is a view in section of the collection plate illustrated in FIG. 5 as seen along line 7—7 thereof;

FIG. 8 is a view in section of the collection plate illustrated in FIG. 5 as seen along line 8—8 thereof;

FIG. 9 is a view in section of the collection plate illustrated in FIG. 5 as seen along line 9—9 thereof;

FIG. 10 is an enlarged view of a portion of the collection plate illustrated in FIG. 9;

FIG. 11 is a view in section of the blood plate illustrated in FIG. 6 as seen along line 11—11 thereof;

FIG. 12 is a view in section of the blood plate illustrated in FIG. 6 as seen along line 12—12 thereof;

FIG. 13 is a view in section of the blood plate illustrated in FIG. 6 as seen along line 13—13 thereof;

FIG. 14 is a view in section of the blood plate illustrated in FIG. 6 as seen along line 14—14 thereof;

FIG. 15 is a view in section of the blood fractionating device illustrated in FIG. 2 as seen along line 15—15 thereof;

FIG. 16 is a view in section of the blood fractionating device illustrated in FIG. 2 as seen along line 16—16 thereof;

FIG. 17 is an end elevational view of the outlet manifold of the blood fractionating device illustrated in FIG. 2;

FIG. 18 is a view in section of the blood fractionating device illustrated in FIG. 2 as seen along line 18—18 thereof;

FIG. 19 is an end elevational view of the inlet manifold of the blood fractionating device illustrated in FIG. 2;

DESCRIPTION OF THE PREFERRED EMBODIMENT

Figure 1:
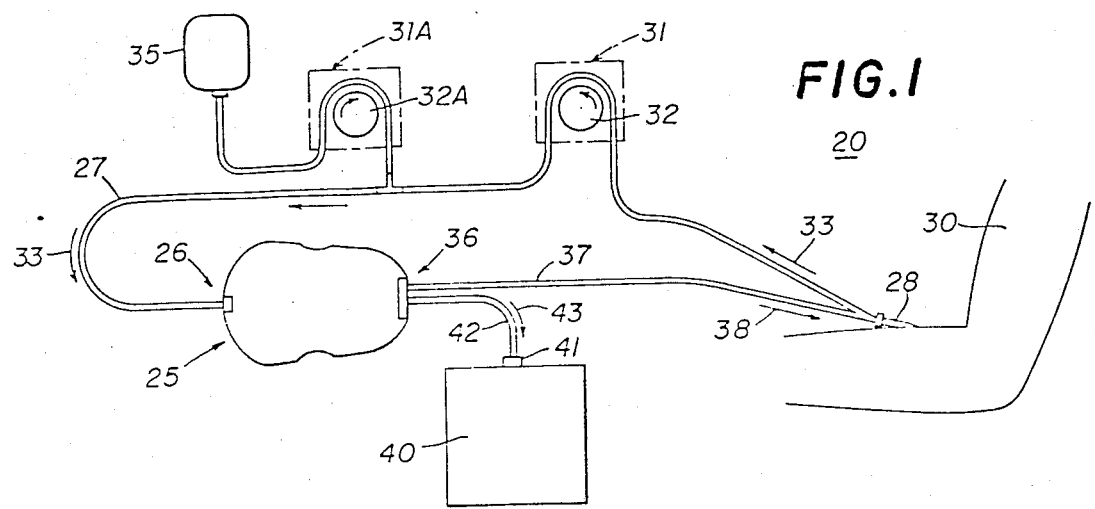
FIG. 1 is a diagrammatic view of the system of the present invention showing the in situ fractionation of blood.

Referring now to FIG. 1 there is illustrated a blood fractionating system 20 which includes a blood fractionator 25 connected in a closed loop to a donor 30. The blood fractionator 25 has an inlet 26 and an outlet 36, the inlet 26 being connected to the donor 30 by a blood tube 27 connected to a catheter, needle or double lumen needle 28 inserted into an appropriate vein or artery of the donor 30. A peristaltic pump 31 having a roller 32 in contact with the blood tube 27 is positioned between the donor 30 and the inlet 26 of the blood fractionator 25 to pump blood from the donor through the tube 27 into the fractionator in the direction of the arrow 33. A supply of anti-coagulant 35 is connected to the tube 27 and the flow rate of the anti-coagulant is modified by a second pump 31A having a roller 32A to provide a predetermined flow rate, as hereinafter explained, of anti-coagulant with the blood flowing from the donor 30 to the fractionator 25. The outlet 36 of the fractionator 25 is provided with a tube 37 which conducts blood in the direction of the arrow 38 to the catheter, needle or double lumen needle 28, thereby to provide the closed loop for the system 20 of the present invention. A blood fraction collection receptacle or bag 40 is provided with a fitting 41 which is connected by a tube 42 to the outlet 36 and more particularly the outlet port 202, see FIG. 18 of the blood fractionator 25 thereby to permit a blood fraction to flow from the outlet 36 in the direction of the arrow 43 to the blood fraction collection bag or receptacle. The pumps 31 and 31A may be of the type disclosed in copending application Ser. No. 672,571, filed Nov. 16, 1984, and entitled "Roller Pump".

Although the blood fractionator 25 of the present invention along with the system 20 disclosed herein may be useful to produce a variety of blood fractions, plasma is one of the most important blood fractions needed in the medical community and, therefore, the blood fractionator 25, as well as the system 20 and method of collecting a blood fraction, will hereinafter be described with respect to blood plasma only, it being understood that other blood fractions may be collected with minor modifications to the device 25 and system 20, as will be apparent to those skilled in the art.

In a preferred embodiment of the present invention, the system 20, with the exception of the pumps 31 and 31A and the anticoagulant bottle 35, may be preassembled as a unit, and may be disposable as a unit after use in the blood fractionation operation. Such a unit may include a suitable spike (not shown) for insertion into the anticoagulant bottle 35. After the blood fraction has been collected in the bag 40, the tube 42 may simply be clamped and severed, so that the filled bag 40 may be retained and the remainder of the unit may be disposed of.

Figure 2:
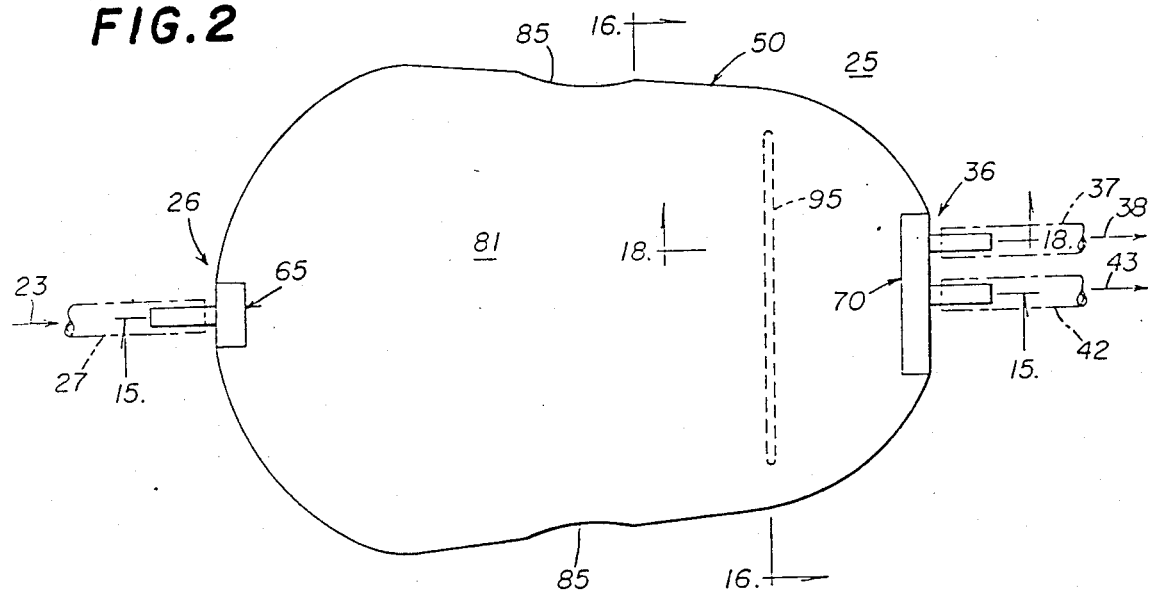
FIG. 2 is an enlarged top plan view of the blood fractionating device illustrated in FIG. 1.
Figure 3:
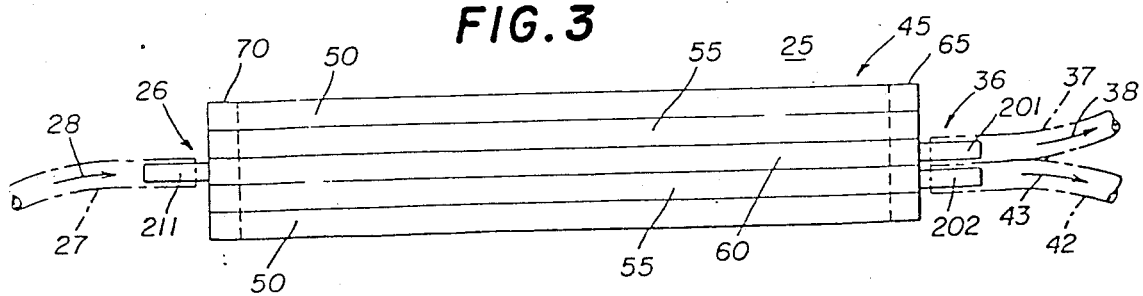
FIG. 3 is a side elevational view of the device illustrated in FIG. 2.
Figure 4:
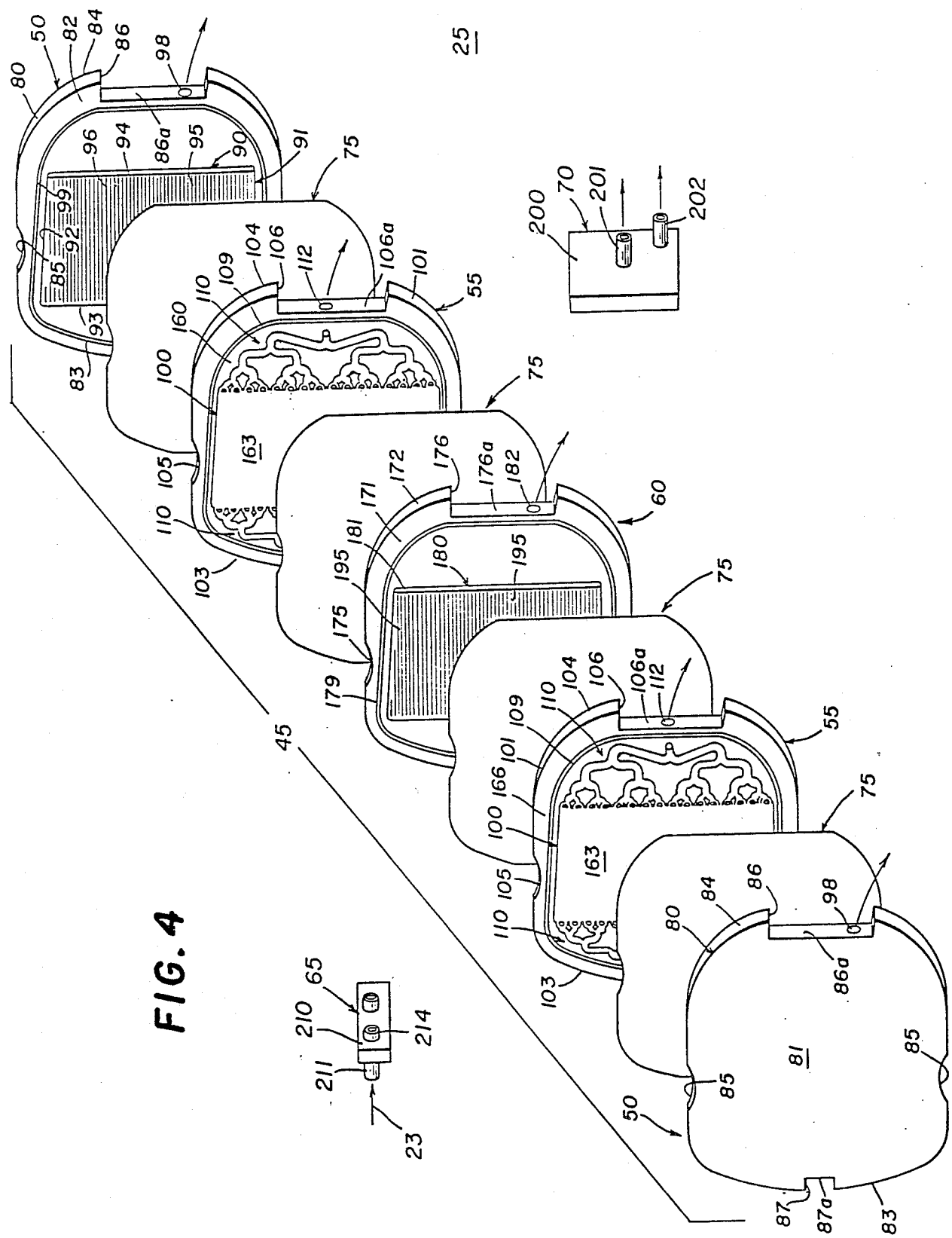
FIG. 4 is an exploded perspective view of the blood fractionating device illustrated in FIG. 1.

Referring now to FIGS. 2, 3 and 4, it will be appreciated that the blood fractionator 25 is made up of a stack 45 of plates, there being provided two external plasma plates 50 two internal blood plates 55 and an interior or internal plasma plate 60, an appropriate inlet manifold 65 and outlet manifold 70 with each of the plasma plates and blood plates being separated by an appropriate membrane 75. As illustrated, the blood fractionator 25 is comprised of a stack 45 of five separate plates and four membranes 75 interleaved between the plates such that each plasma plate 50, 60 faces a blood plate 55 and is separated therefrom by an appropriate membrane 75. It will be appreciated that the stack 45 could as easily be comprised of a stack of plates in which the external plates are blood plates having two double sided plasma plates separated by an internal double sided blood plate. The number of plates also could be increased.

Referirng now to the external plasma plates 50, it will be appreciated that although the plates are not identical, they are mirror images of one another for the sake of brevity like numbers have been placed on like portions of each end plate 50. As seen in FIG. 4 each external plasma plate 50 is an oval member 80 with an outer flat surface 81 opposed by an inner flat surface 82. The plate 50 is generally oval in shape and has a large inlet end 83 and a small outlet end 84. There are opposed recesses 85 in the side edges of the oval member 80 to provide for easy handling and a large notch 86 in the small outlet end 84 having an end surface 86a and a small notch 87 in the large inlet end 83 having a flat end surface 87a.

Each of the end plasma plates 50 has on the inside flat surface 82 thereof a plasma collection channel 90 which has a trapezoidal portion 91 defined by side edges 92 and end edges 93. Toward the small outlet end 84 of the end plasma plate 50 is a transversely extending slot 94 in fluid communication with a plurality of longitudinally extending shallow collection grooves 95 separated by ridges 96. As hereinafter explained, the slot 94 is substantially deeper than the shallow collection grooves 95 and the portion of the grooves 95 adjacent the slot 94 are deeper than the remainder of the grooves 95 but shallower than the slot. A plasma outlet 98 in the form of an aperture extending from the end surface 86a extends through the oval member 80 and is in fluid communication with the slot 94. Finally, an oval tongue 99 surrounds the plasma collection channel 90, for a purpose hereinafter explained.

Referring now to FIGS. 6 and 11 through 14, there is illustrated a blood plate 55 which is provided with the same configuration on both sides thereof, whereby only one side will be described for the sake of brevity. Each of the blood plates 55 is identical in configuration and has in the opposed flat surfaces 102 thereof a blood flow channel 100, the plate 55 being generally oval in shape and identical in size to the external plasma plates 50 previously described. For that matter, all of the plates 50, 55 and 60 have the same general dimensions in plan view. The blood plate 55 has an edge surface 101 and opposed flat side surfaces 102, it being the surfaces 102 in which the blood flow channels 100 are positioned. The blood plate 55 has a large inlet end 103 and a small outlet end 104, with recesses 105 being provided in the side edges as previously discussed with respect to the end plasma plates 50. As in the end plasma plates 50, there is a large notch 106 in the small outlet end 103, the notch having a end surface 106a and there is a small notch 107 at the large inlet end 103, the small notch 107 being provided with an end surface 107a. A groove 109 extends around the periphery of both flat side surfaces 102 and each is complementary in shape to the tongue 99 in the adjacent end plasma plate 50 and are shaped and dimensioned to receive therein the associated tongue 99 as well as the thickness of the membrane 75, as will be explained. Although shown with grooves on blood plate 55 and tongues on plates 50, the tongues and grooves can be interchaned.

Each of the blood flow channels 100 has a distribution portion 110 and a collection portion 110a in the form of a multiple bifurcated manifolds, these distribution and collection portions ae identical in shape but not in dimension, as will be explained, but for the case of brevity again, like numerals have been applied to like portions of the manifolds 110, 110a. Both the distribution portion 110 and the collection portion 110a, that is the bifurcated manifolds are in fluid communication with a transfer portion 160, all for a purpose hereinafter explained.

Referring now to the large inlet end 103 of the blood plate 55, there is an inlet aperture 112 extending through the end surfce 107a of the notch 107 and extending longitudinaly of the blood plate 55. The inlet 112 has a counterbore portion 113 at one end thereof and communicates with an aperture 114 which extends through the plate 55, as best seen in FIGS. 6 and 11, so as to provide communication between the inlet manifold 65 and the blood flow channel 100 on both sides of the plate 55. As notices, the inside facing surface 114a of the aperture 114 is rounded at the juncture with the bifurcated manifold 110 to prevent contact of the blood flowing therethrough with a sharp edge for a purpose, as will hereinafter be set forth.

The manifolds 110 and 110a on each end of the blood plate 55 are multiple bifurcated manifolds in which each path is divided twice and there are five such divisions resulting in a single blood stream entering through inlet 112 being divided into 32 blood streams, as hereinafter set forth, at the delivery end of the manifold 110. Specifically, blood flowing through the aperture 114 enters the blood flow channel 100 at the main channel 115 and there is split at the first bifurcation into two channels 116 with the surfaces 117 being rounded or arcuate so as to prevent the impingment of the blood into corners which results in stagnation and less smooth distribution and flow. Each of the channels 116 curves as at 118 into a secondary channel 119 which is again bifurcated into channels 121, both the arcuate portions 122 and 123 being formed to prevent stagnation and increase smooth flow of blood through the manifold 110. From the channels 121 the blood into the tertiary channel 129 where it is again bifurcated into channels 131 and channels 131 are again provided with arcuate surfaces 132 and 133 for the same purposes as previously described. The blood flows from channels 131 into the fourth tier of channels 149 where they are again bifurcated into channels 141, the channels 141 being provided with smooth arcuate surfaces 142 and 143 to prevent stagnation of blood as it flows through the distribution portion of the blood flow channel 100. A fifth tier channel 149 receives the blood from the channels 141 and is bifurcated as at 151 into two additional streams, thereby making the five bifurcations previously described with each of the channels 151 having rounded or arcuate smooth surfaces 152 and 153 to prevent any stagnation of blood and to enhance the flow characteristics thereof. Each of the bifurcated channels 151 has an entrance 155 to the transfer portion 160 of the blood flow channel 100. As before indicated there are 32 entrances 155 to the transfer portion 160.

As best seen in FIG. 11, the bifurcated manifolds 110, 110a have a continuously changing depth with the manifolds being deeper at the inlet 112 or outlet 112a and being shallower at the junctures with the transfer portion 160 of the blood flow channel 100. It is preferred that this graduation in depth be uniform so that the depth of the manifolds 110, 110a will be the same along a plane transverse to the longitudinally established flow path through the plate 55. Preferably, the varying depth of the manifolds 110, 110a is such that the depth of the manifolds at the juncture with the transfer portion 160 is exactly the same as the depth of the transfer portion.

The transfer portion 160 is generally trapezoidal in plan view and is defined by side edges 161 and end edges 162 with a generally flat uniformly deep surface 163 which is shallow and as hereinbefore set forth of the same depth as the entrances 155 from both the collection and distribution portions of manifolds 110, 110a. Because the transfer portion 160 of the blood flow channel 100 is trapezoidal in shape, that is it tapers from the inlet end 103 to the outlet end 104 of the plate 55, the transverse dimensions of the collection manifold 110a is less than the transverse dimension of the distribution manifold 110. However, the configuration of the collection manifold 110a is precisely the same as the configuration of the distribution manifold 110; therefore, like numerals have been placed on like portions to prevent repetitive description. Suffice it to say that the entrances 155 of the collection manifold 110a at the end of the transfer portion 160 are identical in configuration and number but smaller in overall transverse dimension than the entrances 155 from the manifold 110. The same five bifurcations are in the manifold 110a as in the manifold 110 and the vertically extending aperture 114 with the same arcuate surface 114a connects the outlet 112a to the collection manifold 110a, the outlet 112a being provided in the end edge 106a of the notch 106 and having a counterbore portion 113a of the same size and dimension as the counterbore 113 at the inlet end 103.

Similarly, the collection manifold 110a has a varying depth in the same manner as the distribution manifold 110, that is the depth of the entrances 155 is the same as the depth of the transfer portion 160 and the depth of the manifold increases uniformly from the entrances 155 toward the aperture 114. Again, the increase in depth is preferably uniform so that the depth of the manifold 110a would be exactly the same along a plane transverse to the longitudinally established blood flow path of the blood plate 155.

Accordingly, it is seen that the blood plate 55 has provided blood flow channels 100 on both sides thereof and each blood flow channel 100 is identical and has a distribution portion in the form of a multiple bifurcated manifold 110, a transfer portion 160 and a collection portion in the form of a multiple bifurcated manifold 110a. The blood flow is established longitudinally of the plate and flows from the inlet 112 through the end surface 107a of the notch 107 and exits through the outlet 112a through the end surface 106a of the notch 106 which is opposite to the notch 107.

The multiple bifurcations of the manifolds 110 and 110a are most easily seen in reference to FIGS. 12 and 14. FIG. 12 is taken along a portion of the manifold 110 where there are four channels 129 and FIG. 14 is taken along the entrances 155 of the manifold 110 wherein there are thirty-two channels. As seen therefore, the blood flow has been bifurcated five times so that from a single blood stream at the inlet 112 it is divided twice five times, there being two channels 116, four channels 121, eight channels 131, sixteen channels 141 and thirty-two channels 151 which terminate in the entrances 155.

These five bifurcations repeated on the collection manifold 110a to combine, in a uniform manner, the thirty-two streams entering the collection manifold 110a from the transfer portion 160 to a single outlet stream in the outlet 112a. FIG. 13 clearly illustrated the two transfer portions 160 of the blood flow channel 100 which consist of a shallow trapezoidal shaped groove, the trapezoidal shape being for a purpose hereinafter set forth.

Referring now to FIGS. 5, 7-10, there is shown the internal plasma plate 60 having the same configuration on both sides of the plate and more particularly the plate 60 has opposed flat surfaces 171 and a peripheral edge surface 172. There is a large end 173 which corresponds to the inlet 26 and a small end 174 which corresponds to the outlet 36. In the side of the edge surfaces 172 are two finger recesses 175 of the same size and dimension as the previously described recesses 85 and 105. At the outlet end 36 corresponding to the small end 174 is a large notch 176 of the same size and configuration as the previously described notches 86 and 106 respectively in the end plasma plates 50 and the blood plates 55. The large notch 176 has an end surface 176a. Opposite the large notch 176 is a smaller notch 177 in the inlet 26 of the device 25 which corresponds to the small end 173 of the plate 60. Notch 177 is of the same size and dimension as the previously described notches 87 and 107 and is provided with an end surface 177a. A tongue 179 extends around the periphery of each side surface 171 of the plate 60 and is constructed and arranged to fit within one of the notches 109 in the blood plates 55.

A plasma collection channel 180 is in both side surfaces 171 of the plate 60 and is of the same size and dimension and is similarly constructed to the plasma collection channel 90 in the end plasma plates 50. Specifically, the plasma collection channel 180 includes a slot 181 which extends entirely through the plate 60 and opens onto both opposed substantially flat surfaces 171. An aperture 182 forms the plasma outlet which extends through the surface 176a of the notch 176 and has a counterbore area 183 for receiving a suitable fixture from the tubing 42 which leads to the plasma collection receptable or bag 40. It is noted that in plan view, the plasma outlet 182 is in vertical alignment with the plasma outlets 98 of the end plasma plates 50; however, in FIG. 5 the plasma plate 60 is reversed so that while it appears the plasma outlet 182 is displaced, it is seen, particularly from FIG. 4, that the plasma outlet 182 is aligned with each of the other plasma outlets 98 of the end plasma plates 50, for a purpose hereinafter described.

The plasma collection channel 180 further includes a trapezoidally shaped collection area 185 defined by side edges 186 and end edges 187, the trapezoidal plasma collection area being substantially the same size and dimension as the transfer portion 160 of the blood plates 55 and the same as the trapezoidal plasma collection portion or area 91 of the end plasma plates 50. As with the end plasma plates 50, there are a plurality of longitudinally extending shallow collection grooves 195 separated by ridges 196. Immediately adjacent the transversely extending slot 181 is a portion 197 of the grooves 195 which is deeper than the remainder of the grooves 195 but of course shallower than the slot 181 which extends entirely through the plate 60.

As seen, therefore, the blood fractionator 25 is comprised of a stack 45 of alternating blood plates 55 and plasma plates 50, 60 interleaved by membranes 75. The membrane 75 is selected so that the pore size of the membrane selectively passes the blood fraction to be collected. In the case of a plasma collection device, the membrane 75 preferably has a pore size in the range of rom about 0.1 microns to about 1.5 microns. Membranes are commercially available with pore sizes 0.6 microns, 0.65 microns and 1.0 microns. Others may be available. Nuclepore, Gelman, Millipore and Sartorius produce membranes suitable for blood plasma harvesting. Other blood fractions which are of interest and which may be separated by the fractionator 25 are protein-free filtrates and protein fractions and membranes useful for these purposes would necessarily have pore sizes in the range of from about 50 Angstrom to about 0.05 microns. These membranes, also are readily available as will be appreciated by those skilled in the art.

The stack 45 is sealed in part and clearly aligned by the tongue and groove mechanism previously described. For instance, the end plasma plates 50 have the tongues 99 while the blood plates 55 are provided with the grooves 109 and the central plasma plate 60 has the tongues 179, all of which are shaped, constructed and arranged to fit one within the other while accommodating therein membrane 175 which, as illustrated in FIGS. 15-18, extends from edge to edge of the various plates. The usefulness of the tongue and groove construction is that the membranes 75 remain imperforate which is critical to the design of the blood fractionator 25 and to the operation of the system 20 since membrane rupture or leakage can result in serious problems. Furthermore, an imperforate membrane effectively constructs blood flow channels without the need for gaskets or other fluid separating components. In any event, utmost care is taken to ensure the leak free nature of the membranes 75 and to this end, the design of a device which provides an imperforate membrane 75 is a significant advantage.

Completing the blood fractionator 25 and coacting with the stack 45 are the blood inlet manifold 65 and the blood and plasma outlet manifold 70. The function of the blood inlet manifold is extremely important and is to uniformly distribute the blood from the donor 30 which enters the blood fractionator 25 through the inlet 26 and particularly through the tube 27 among the blood plates 55. In the preferred embodiment, there are two blood plates 55, whereby the function of the blood inlet manifold 65 is to uniformly distribute the blood flow from the donor 30 evenly between the two blood plates 55 and specifically to the respective inlets 112 of each plate leading to the associated multiple bifurcated manifolds 110. The blood inlet manifold 65 is received in the aligned series of notches 97, 107 and 177 and, as best seen in FIG. 19, the blood inlet manifold is comprises of a solid block, preferably of plastic 210, having a blood inlet port 211, a bifurcated passageway 213 and two fitting 214 of a size and dimension to fit snugly within the counterbore portion 113 of each blood plate 55.

Referring now to the blood and plasma outlet manifold 70 illustrated particularly in FIGS. 4, 15 and 17, there is a block, preferably of plastic 200 which has a blood outlet port 201 connected to the tubing 37 so that blood flowing from the blood fractionator 25 in the direction of the arrow 38 returns to the donor 30. The blood outlet port 201 is in fluid communication with a bifurcated passageway 203 which leads to two fittings 204 constructed and arranged to fit within the counterbore portions 113a of the two blood plates 55. The block 200 like the block 210 is constructed and arranged snugly to fit within the appropriate opening formed by the series of notches 86, 106 and 176 of the stack 45 of plates. The outlet manifold 70 also has a plasma outlet port 202 connected to the tubing 42 which permits plasma to flow in the direction of the arrow 43 into the plasma collection receptacle or bag 40.

The plasma outlet port 202 is connected to a trifurcated passageway 206 which has connected thereto two end fittings 207 and a center fitting 208 respectively fitting into the counterbore portions of the plasma end plate outlets 98 and the counterbore portion 183 of the interior plasma plate 60. The fit of the inlet manifold 65 and the outlet manifold 70 is such as to provide a fluid tight fit between the manifold and the appropriate portions of each plate, thereby to ensure no leaks during operation. It will be appreciated that the plates are maintained in their stacked configuration by the two manifolds 65 and 70 which may fixedly secured to their respective series of notches by a suitable adhesive which is biocompatible with blood and blood components or by ultrasonic welding or other methods well known in the art.

In the plasma harvesting art, there has been a long felt need to provide an easier, safer, more economical method of harvesting plasma than that which is commercially available. There has been a significant amount of money both from the private sector and from the government dedicated to finding solutions to the problem, but as of yet there has been no satisfactory solution. Problems encountered in the art are many but the most significant problem is the rapid degradation in plasma production with time for any device heretofore discovered or proposed. It is not unusual to have initial plasma production that is significant and commercially acceptable however within a relatively short time, in the order of less than a half hour, plasma production falls off so dramatically that as of the present date no commercial device is available which meets the criteria heretofore set forth.

The present blood fractionator 25 and system 20 meet all the criteria set forth above and provides commercially acceptable plasma collection rates even after more than one half hour of continuous plasma production. When harvesting blood with a 5-plate embodiment, it is preferable that the blood flow rate from the donor 30 to the blood fractionator 25 be in the range of from about 50 milliliters per minute to about 100 milliliters per minute. Blood flow rates above 100 milliliters per minute do not significantly augment plasma flow unless additional plates are added, whereas flow rates less than about 50 milliliters per minute result in low plasma production. Clearly, blood hematocrit affects the amount of plasma produced with higher hematocrit values producing less plasma due to lower filtration rate.

In human donors it is usual to encounter hematocrit values in the range of from about 38 to about 55 percent. The taper of the plates in the stack 45 has been calculated on the basis on a average hematocrit value of about 45 percent and is also determined, to some extent, by the length of the blood flow path and particularly by the length of the trapezoidal area of the various plates. The taper is used to maintain constant the blood flow rate as plasma transfers through the membrane 75 thereby decreasing the volume of the blood. It is also important to maintain shear constant and the taper also accomplishes this purpose. In the blood fractionator 25 described, the calculated blood flow velocity which was maintained substantially constant due to the construction of the device was about 5.7 centimeters per second with a mean shear of 6027 sec$^{-1}$.

In addition to the tapered blood channel to maintain constant velocity and shear, it was also discovered that in order to obtain commercially acceptable plasma collection rates over a substantial period of time, it was beneficial to provide entry acceleration of the blood from the manifold to each plate and this, of course, is provided by the inlet manifold 65. An additional important feature of the fractionator 25 is the progressive decrease in the bifurcated manifold channel depth from entry to exit, this referring to the bifurcated manifolds 110 in each of the blood plates 55.

Still another important feature of the blood fractionator 25 is the shallow parallel grooves 195 in the plasma plate 60 and the similar grooves 95 in the end plates 50 which function to optimize transmembrane pressure and to minimize flow resistance to plasma during operation of the fractionator 25. The optimization of the transmembrane pressure greatly reduces the rate at which red blood cells plug the pores of the membrane 75.

Still another important feature of the system 20 and the fractionator 25 is the vertical inlet manifold 65 and outlet manifold 70 which, in cooperation with other design features of the fractionator, result in a uniform blood distribution intraplate and a uniform blood distribution along each blood flow channel 100. Another aspect of the inlet manifold 65 and the outlet manifold 70 which coopertes with tongue and groove construction of the fractionator 25 is the elegant seal of the device 25 which simplifies the internal gasketing necessary to maintain a liquid tight seal for the fractionator 25.

In a constructional example of the fractionator 25, each of the plates 50, 55 and 60 is 0.19 inches thick. The width at the section 12—12 is 3.0 inches, the width at section 13—13 is about 3.04 inches and the width at section 14—14 is about 2.85 inches. The overall length of the fractionator, absent the inlet 211 and the outlet 201 is about 4.89 inches and the overall width at its widest part is about 3.38 inches. The dimension of the blood transfer portion 160 of the blood transfer plate 145 is about 3.0 inches at its widest and about 2.2 inches and its narrowest, this representing a taper in the order of about 8°.

It should be understood that the taper is calculated on the basis that plasma transfer through the membrane 75 is uniform throughout the blood transfer portion 160 and on the length of the portion 160. For longer devices, the taper is necessarily greater and tapers of up to about 10° are contemplated. The length of the blood transfer area 160 is about 2.6 inches.

The passageway 114 which connects the inlets 112 with the multiple bifurcated manifold 10 has a diameter of about 0.125" and the entrances 155 are each about 0.031" wide and are spaced about 0.093", center to center at the large end and 0.069" center to center at the small end.

Referring now to the plasma plates and particularly to FIGS. 9 and 10 the depth of the longitudinally extending shallow grooves 195, and for that matter the grooves 95, are preferably about 3 mils. Each of the grooves 95, 195 as best seen in FIG. 10, are described by an arc 62 mils in radius and each of the ridges 96, 196 are about 46 mils center to center. The depth of the portions 197 of the grooves 195 and the portions of the grooves 95 unnumbered immediately adjacent the respective slots, 94, 181, have a depth of about 0.052". This portion of the grooves is important because it decreases flow resistance as the plasma or blood fraction flows into the slots. Preferably, for grooves 95, 195, 3 mils deep, the portion 197 would be in the range of from about 0.04" to about 0.07". Less than about 0.04" would not accomplish the required reduction in blood fraction or plasma flow resistance while greater than about 0.07" would enhance clogging by red cells.

Another feature of the blood fractionator 25 is the continuously decreasing depth of the multiple bifurcated manifolds 110, 110a from the inlet 112, outlet 112a to the blood transfer area 160. This is important because blood exits the multiple bifurcated manifold 110 and particularly the entrances 155 with a slight inclination toward the surface of the adjacent membrane 75 which seems to be an advantage to the present design. Because relatively high shear is important to prevent the membrane 75 from clogging with red blood cells, the blood flow channel was kept shallow. As channel height was increased, filtration rate decreased.

Summarizing, there are a number of factors which apparently cooperate to enable a commercial device to be made which operates satisfactorily and which meets all the objects of the present invention. Of the most important features of the present invention are the uniform intraplate distribution of blood by the inlet manifold 65, the uniform transverse distribution of blood across the plates by the multiple bifurcated manifolds 110, the uniform flow velocity and shear accomplished by means of the tapered transfer areas 160, the shallow blood flow path accomplished by the depth of the transfer areas 160 and the immediately adjacent membrane 75, the optimization of transmembrane pressure by the shallow grooves 95, 195 of the plasma plates 50, 60, the reduction in the flow resistance of the plasma due to the increased depth of the grooves 195 at the portions 197 and the like portions on the end plasma plates 50, the uniform collection of the plasma by the outlet manifold 70, and the uniform condensation of the multiple streams into a single outlet stream by the multiple bifurcated manifold 110 at the outlet end 36 of the fractionator 25 and the use of a design which obviates the necessity for internal gaskets or perforations of the membrane.

Reported hereafter in Tables I, II and III are data obtained with in vitro experiments with human blood. Because of the nature of stored human blood, the hematocrit value was adjusted to 33 percent with saline. In Table I and III, a single membrane device was used and hence the blood flow rate was 20 milliliters per minute whereas Table II reports a five layer, four channel device wherein the total blood flow rate was 80 milliliters per minute. Several different design modifications are shown. Accordingly, in order to extrapolate the initial and final filtrate rates reported in Tables I and III, these values must be multiplied by four.

TABLES I, II AND III

TABLE I

B00191/P00181 Results
All experiments in vitro with human blood, hematocrit adjusted to 33 per cent with saline.
Pump speed = 20 ml/minute

| Number Experiments | Membrane | Inlet Pressure mm Hg | Outlet Pressure mm Hg | Initial Filtrate ml/min | Final Filtrate ml/min |
|---|---|---|---|---|---|
| 7 | Nuclepore 0.6 u | 244 | 25 | 6.2 | 4.3 |
| 6 | Nuclepore 1.0 u | 275 | — | 7.5 | 6.8 |
| 4 | Gelman 0.65 u | 404 | — | 8.2 | 6.8 |

TABLE II

B00191/P00181 Results
All experiments in vitro per Table I.
Pump speed = 80 ml/min.
Five layers with 4 blood channels in parallel.

| Number Experiments | Membrane | Inlet Pressure mm Hg | Outlet Pressure mm Hg | Initial Filtrate ml/min | Final Filtrate ml/min |
|---|---|---|---|---|---|
| 8 | Nuclepore 0.6 u | 215 | — | 26.1 | 12.9 |
| 1 | Nuclepore 1.0 u | 96 | — | 20.5 | 15.5 |
| 12 | Gelman 0.65 u | 239 | — | 25.0 | 20.9 |

TABLE III

B00198/P00188 Results
All experiments in vitro per Table I.
Pump speed = 20 ml/min. Single layer.

| Experiments | Membrane | Inlet Pressure mm Hg | Outlet Pressure mm Hg | Initial Filtrate ml/min | Final Filtrate ml/min |
|---|---|---|---|---|---|
| 6 | Nuclepore 0.6 u | 154 | — | 4.6 | 3.1 |
| 2 | Nuclepore 1.0 u | 189 | — | 7.3 | 6.5 |
| 4 | Gelman 0.65 u | 190 | — | 4.4 | 2.1 |

Table IV reports the results of various dog experiments, it being noted that fresh blood produced a significantly higher final plasma flow rate than did the stored blood used in the experiments reported in Tables I–III.

TABLE IV

Dog experiments with B00191/P00181
Blood pumped from femoral artery and returned to femoral vein.
Citrate pumped into entry blood line prior to entry into device.

| Blood Channel Height-In. | Membrane | Dog | Blood Flow ml/min | Citrate Flow ml/min | Total Flow ml/min | Average Plasma Flow ml/min | Initial Plasma Flow | Final Plasma Flow |
|---|---|---|---|---|---|---|---|---|
| .003 | Nuclepore 0.6 u | 1 | 58 | 22 | 80 | 21.3 | 22.5 | 18.0 |
| .003 | Nuclepore 0.6 u | 1 | 58 | 22 | 80 | 19.3 | 20.5 | 17.0 |
| .003 | Nuclepore 0.6 u | 1 | 58 | 22 | 80 | 17.9 | 18.5 | 17.5 |
| .003 | Nuclepore 0.6 u | 2 | 58 | 22 | 80 | 22.6 | 24.0 | 22.0 |
| .0045 | Gelman | 2 | 58 | 22 | 80 | 16.9 | 17.5 | 17.0 |
| .003 | Gelman | 2 | 58 | 22 | 80 | 30.8 | 35.0 | 28.0 |
| .003 | Gelman | 3 | 70 | 10 | 80 | 21.6 | 25.5 | 17.0 |
| .003 | Gelman | 3 | 70 | 10 | 80 | 21.1 | 24.5 | 19.0 |
| .0045 | Gelman | 3 | 70 | 10 | 80 | 11.1 | 11.5 | 10.5 |
| .003 | Gelman | 3 | 58 | 22 | 80 | 25.3 | 28.0 | 24.0 |

TABLE IV-continued
Dog experiments with B00191/P00181
Blood pumped from femoral artery and returned to femoral vein.
Citrate pumped into entry blood line prior to entry into device.

| Blood Channel Height-In. | Membrane | Dog | Blood Flow ml/min | Citrate Flow ml/min | Total Flow ml/min | Average Plasma Flow ml/min | Initial Plasma Flow | Final Plasma Flow |
|---|---|---|---|---|---|---|---|---|
| .003 | Nuclepore .65 u | 3 | 58 | 22 | 80 | 21.9 | 25.0 | 20.5 |

Table IV also illustrates certain results with blood flow channels having depths of 3 mils and 4.5 mils, but as seen from the data significant differences were not seen. For a single membrane device of the type reported in Tables I–III, typical manifold entrance velocities at 114 were 4.2 centimeters per second and typical manifold exit velocities at 155 were 17.4 centimeters per second. The blood flow channel velocity was, as previously reported, 5.7 centimeters per second and the blood channel mean shear was 6,027 $sec^{-1}$. The manifold 110 flow channels, at the inlet were approximately 125 mils deep with the depth decreasing progressively, and uniformly, to 3 mils at the juncture between the ends of the manifolds 110 and the beginnings of the blood transfer area 160 on the one hand and the entrance to the manifold and the end of the blood transfer area on the other hand.

In the blood fractionator 25 as illustrated, there are five plates with four blood-fraction plate pairs separated by four sheets of membrane. It is clear that larger or smaller stacks may be used without departing from the scope of the invention.

As illustrated, the system 20 is useful to provide a method of continuously fractionating blood in situ, that is continuously fractionating blood utilizing a closed loop system with a donor 30. The closed loop consists of the tubes 27 and 37 in combination with the double lumen needle, needles or catheter 28 and the blood fractionator 25 enabling a method to be used in which blood is continuously pumped via the pump 31 from the donor 30 in a closed loop through the blood fractionator 25 and returned to the donor. The blood fraction is continuously produced during the operation of the method and is collected in the receptacle or blood fraction bag 40. The method optimizes transmembrane pressure resulting in continued satisfactory blood fraction collection rates for prolonged durations. The method also includes the use of an anti-coagulant 35 which may be citrated saline or heparinized saline, or other well known anti-coagulants. The flow rate of the anti-coagulant and the blood are fixed by the pumps 31 and 31A used in conjunction with the supply 35 of anti-coagulant. A flow rate of 65 milliliters of blood per minute and 15 milliliters of anti-coagulant per minute for a total inlet flow rate to the fractionator 25 of about 80 milliliters per minute has been satisfactory.

By the design of the fractionator 25, the blood velocity is maintained constant through the transfer area of each plate, but the blood velocity is accelerated from manifold inlet to manifold outlet. In addition, the blood shear is also maintained substantially constant from manifold inlet to manifold outlet.

The system 20 of the present invention, as previously described, may have other safety features not illustrated. For instance, an air bubble detection device may be included on the return tubing 37 and there may be a blood leak detector or other such equipment elsewhere located in the system, all well within the skill of the art.

An important and unique feature of the blood fractionator 25 is the minimum volume of the device. All of the blood channels of the device 25, including both end manifolds 110, 110a, have a volume less than 2.5 ml. volume of the plasma compartments, including manifolds, is less than 2 ml. This feature, not present in previously described devices, minimizes blood loss by the donor and maximizes plasma recovery. The minimal amounts of plasma left in the device 25 are important to commercial utilization of the device. Accordingly, low blood and plasma retention volumes of less than 10 mls is an important commercial feature of the invention. Total blood volume of the tubing plus fractionator 25 is estimated to be less than 20 ml.

Total membrane area of the device is 176 $cm^2$ whereas previously described devices may use as much as 10,000 $cm^2$ of membrane. The reduction of membrane area contributes significantly to reduction of costs. This is a substantial improvement over prior art devices which require larger quantities of membrane, thereby resulting in a substantially more expensive device, not suitable for a disposable device.

Figure 20:
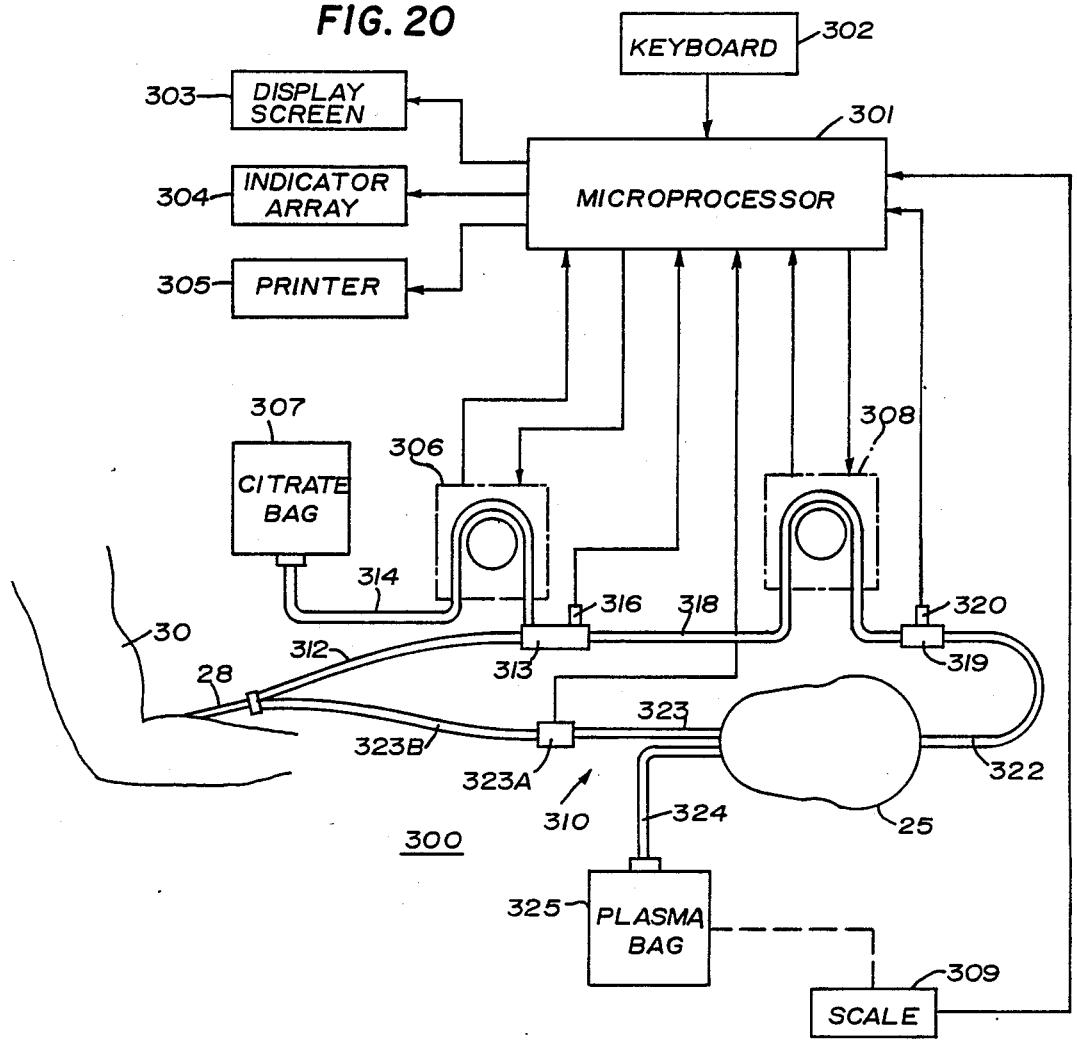
FIG. 20 is a diagrammatic view of an automatic system in accordance with the present invention for performing the method of the present invention wherein the method is customized for individual donors.

An important aspect of the present invention is that the blood fractionating system 20 and the blood fractionator 25 thereof are uniquely adapted for use in an automated system which can be easily tailored or customized for each individual donor. Referring to FIG. 20 there is illustrated such an automated system, generally designated by the numeral 300. The system 300 includes a microprocessor 301 coupled to a keyboard 302 for selectively inputting information to the microprocessor 301, along with a display screen 303, an indicator array 304 and a printer 305 for outputting information from the microprocessor 301. The system 300 also includes an anticoagulant pump 306 for pumping anticoagulant from an associated source, such as a citrate bag 307 and a blood pump 308, the pumps 306 and 308 being substantially identical to the pumps 31 and 31A described above in connection with FIG. 1. A scale 309 is provided for weighing the collected plasma, the scale 309 being coupled to the microprocessor 301 for transmitting weight information thereto.

Figure 23:
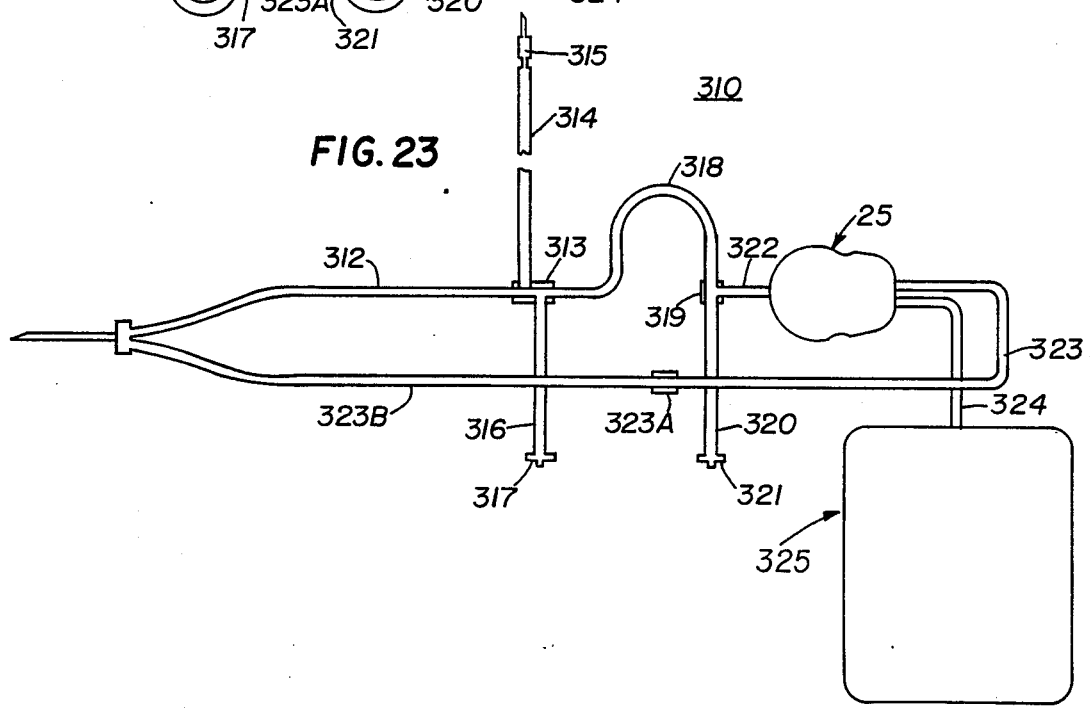
FIG. 23 is a plan view of the disposable parts of the system of FIG. 20.

Referring also to FIG. 23, the system 300 also includes a disposable fractionator unit 310, which is similar to the fractionator system 20 described in connection with FIG. 1. The disposable fractionator unit 310 includes a catheter or double lumen needle 28 adapted to be inserted into the donor's arm 30, and having a collection leg coupled to one end of a supply tube 312. The other end of the tube 312 is coupled to one input of a mixer 13, which has another input connected to one end of an anticoagulant tube 314. Connected to the free end of the tube 314 is a spike 315 for insertion in the citrate bag 307. The mixer 313 has a monitoring port which is coupled to one end of a pressure line 316, the other end of which is provided with a coupler 317. The output of the mixer 313 is coupled to one end of a tube 318, the other end of which is coupled to the input of a T-fitting 319.

The fitting 319 has a monitoring port which is coupled to one end of a pressure line 320, the other end of which is provided with a coupler 321. The outlet of the fitting 319 is connected to one end of a tube 322, the other end of which is coupled to the inlet of the blood fractionator 25. The blood outlet port of the fractionator 25 is coupled to one end of a tube 323, the other end of which is coupled to the inlet end of a bubble detector 323A. The outlet of the bubble detector 323A is coupled to one end of a tube 323B, the other end of which is adapted to be coupled to the return leg of the double lumen needle 28. The plasma outlet port of the fractionator 25 is coupled to one end of a tube 324, the other end of which is coupled to the inlet of a plasma bag 325.

Figure 24:
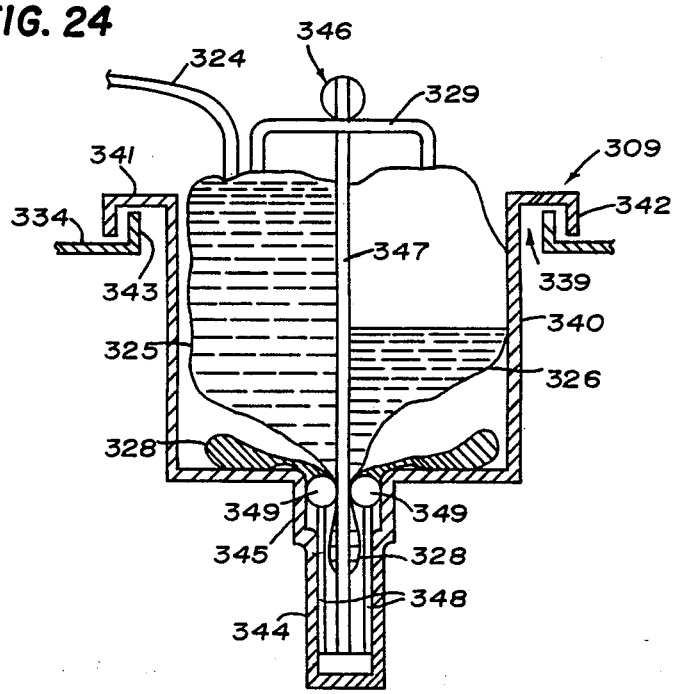
FIG. 24 is an enlarged fragmentary view in vertical section, taken generally along the line 24—24 in FIG. 22, with plasma bags in place.

The plasma bag 325 may be of the type illustrated in FIG. 24, and will preferably be packaged with a second bag 326, which may be needed for donors weighing over 167 pounds. The second bag has a spike assembly including a tube 329 adapted to be coupled to a nipple in the bag 325 to provide an overflow connection between the bags 325 and 326 when both are used. It will be appreciated that the disposable fractionator unit 310, which includes all of the structure in FIG. 23, is preassembled as a unit and, after use, the plasma bag 325 may be separated and the remainder of the fractionator unit 310 may be disposed of.

Figure 21:
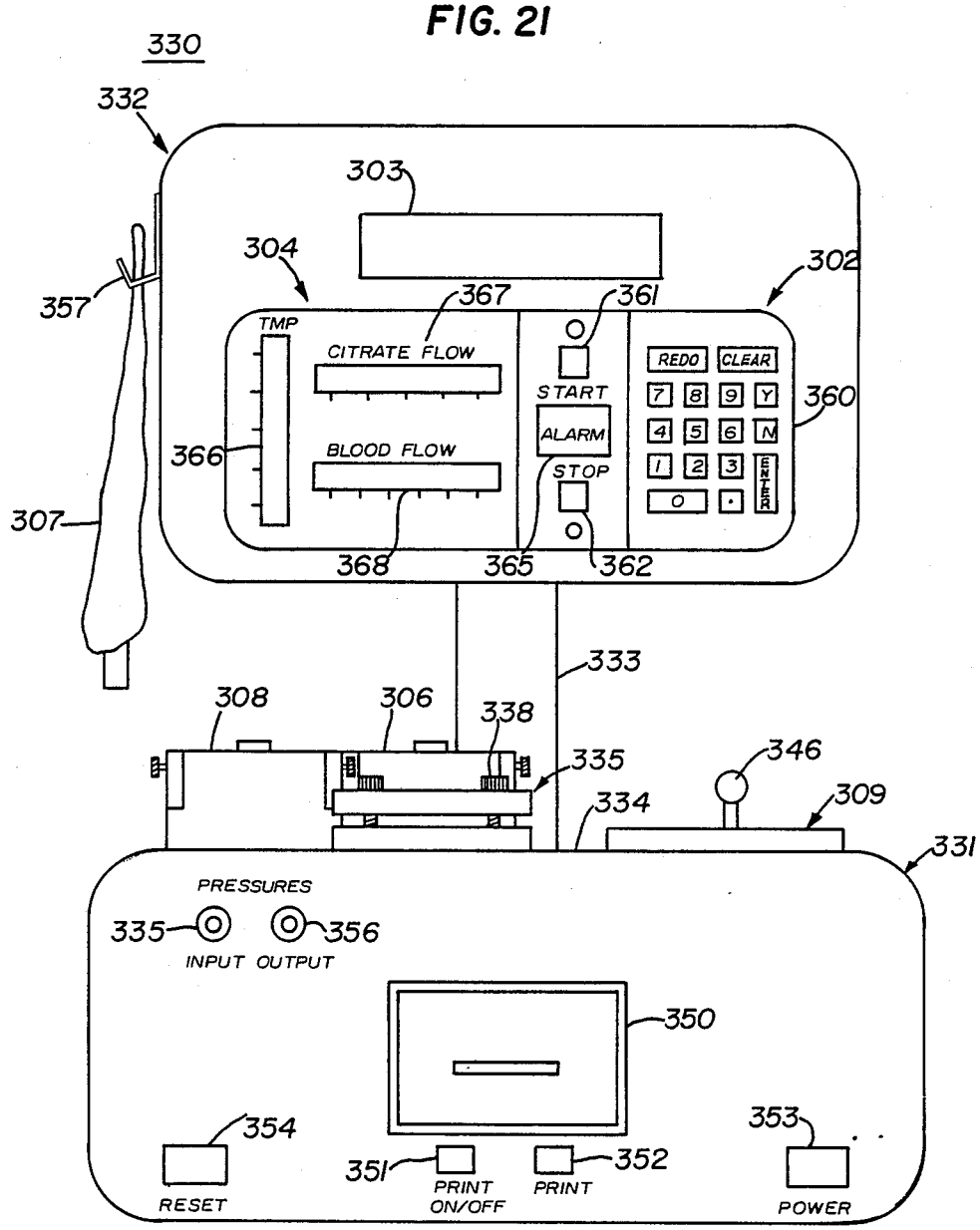
FIG. 21 is a front elevational view of the console unit of the system of FIG. 20.
Figure 22:
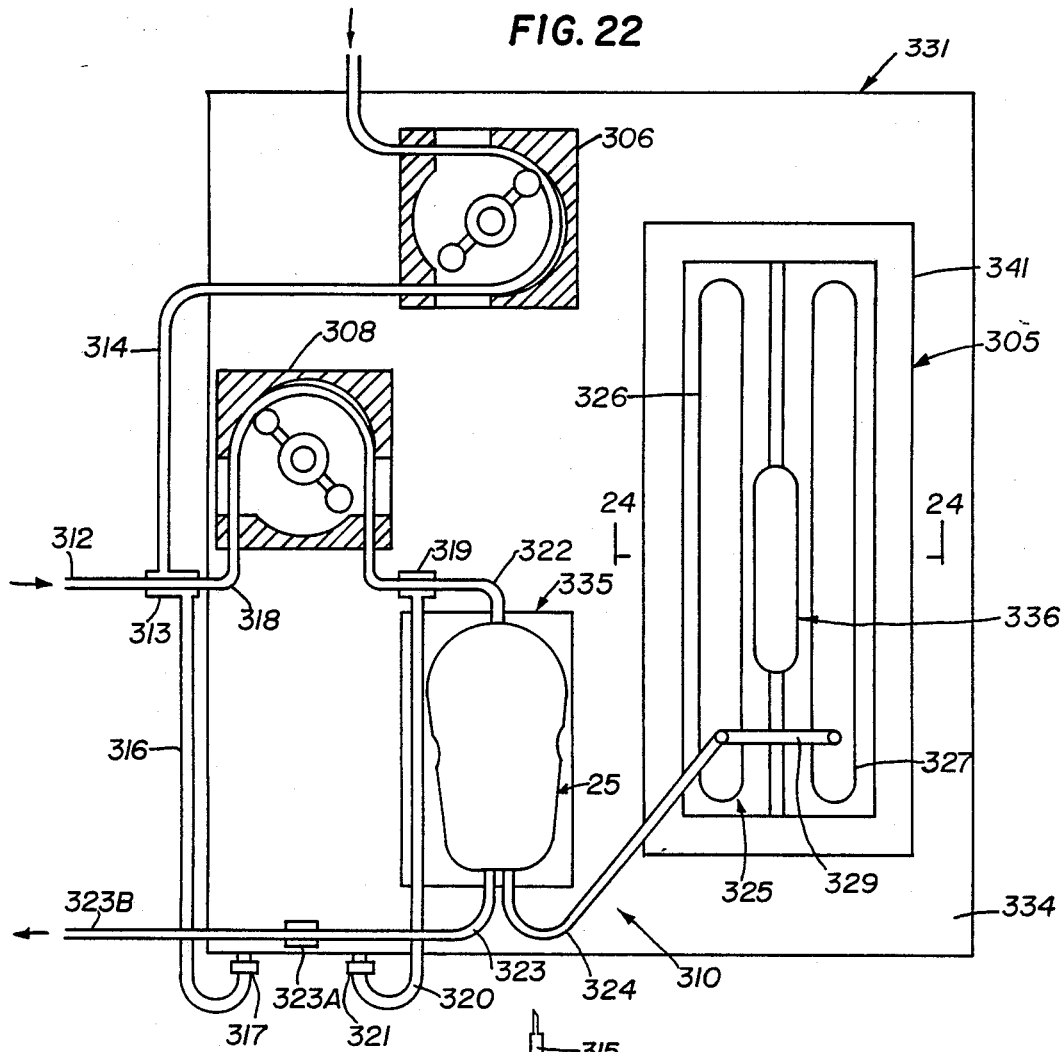
FIG. 22 is a top plan view of the lower housing of the console unit of FIG. 2, with disposable parts in place.

Referring also to FIGS. 21 and 22, the system 300 includes a console unit 330 comprising a lower box-like housing 331 and an upper box-like housing 332, mounted above the rear end of the lower housing 331 by means of a vertical support post 333. Preferably, the printer 305, the scale 309, motors for the pumps 306 and 308, a power supply, and pressure transducers are all mounted within the lower housing 331, while the pumps 306 and 308 are mounted on the top wall 334 of the lower housing 331 externally thereof. The microprocessor 301, the keyboard 302, the display screen 303 and the indicator array 304 are all mounted in the upper housing 332, interconnections between the lower and upper housings 331 and 332 being provided through the support post 333, which may be hollow.

Also mounted on the top wall 334 of the lower housing 331 is a fractionator holder 335, which includes a lower plate 336 fixedly secured to the top wall 334 and an upper plate 337 which is disposable above the lower plate 336 for cooperation therewith to clamp the fractionator 25 therebetween, the parts being secured in place by fasteners 338. Formed in the top wall 334 of the lower housing 331 is a large rectangular opening 339 (see FIG. 24), in which the scale 309 is mounted. The scale 309 includes a receptacle 340 which is generally in the form of an open-top rectangular box. Integral with the side walls of the receptacle 340 at the upper end thereof and extending laterally outwardly therefrom substantially perpendicular thereto around the entire perimeter thereof is a support flange 341, which is provided at its outer edge with a depending retaining flange 341 extending around the entire circumference thereof.

In use, the receptacle 340 fits in the opening 339 with the support flange 341 overlying the upper edge of an upstanding lip 343 on the lower housing top wall 334 around the entire perimeter of the opening 339. It will be appreciated that the retaining flange 342 cooperates with the lip 343 to provide a splashproof interlock to prevent any loose liquid in the receptacle 340 from falling through the opening 339. As can be seen in FIG. 24, the receptacle 340 is suspended above the lip 343, being resiliently supported in any suitable manner on the scale 309. The bottom wall of the receptacle 340 is provided with a depending rectangular clamp well 344, the upper end of which is widened, as at 345. A clamp 346 is adapted to be disposed in the clamp well 344, and includes a rectangular main plate 347, the lower end of which carries a pair of pivoting wings 348 respectively disposed on the opposite sides of the main plate 347. Each wing carries at its distal end a gripping bead 349, substantially circular in transverse cross section. The receptacle 340 and clamp 346 may be of the type disclosed in copending U.S. application Ser. No. 684,020, filed Dec. 20, 1984, and entitled "Bag Clamping Device to Automatically Control Volume and Overflow".

In use, the plasma bags 325 and 326 are respctively disposed on opposite side of the main plate 347 of the clamp 346. Each bag is folded in half and the folds are inserted between the main plate 347 and the wings 348, which are then pivoted up for cooperation with the main plate 347 to clamp therebetween the folds. Then the clamp 346 is inserted in the clamp well 344, which is dimensioned so that the gripping beads 349 are interference fitted in the widened upper end 345 of the well 344, with the wings 348 being disposed snugly along the inner surfaces of the well 344.

Refering now to FIG. 21, the front wall of the lower housing 321 is provided with a printer output 350 which may emit a printed paper tape, or the like. Also mounted on this front panel are on ON-OFF switch button 51 and a control switch button 352 for the printer, as well as a power switch button 353 and a reset switch button 354 for the system 300. Also mounted on this panel are Luer connectors 355 and 356 for respectively receiving the couplers 317 and 321 of the pressure lines 316 and 320, the connectors 355 and 356 being coupled to suitable pressure sensors (not shown) inside the lower housing 331.

The upper housing 322 carries on its side wall a bag holder 357 on which the citrate bag 30 can be hung. Mounted in suitable openings in the front panel of the upper housing 332 for viewing and access by a user are the keyboard 302, the display screen 303 and the indicator array 304. The keyboard 302 includes a key pad 360 as well as a START switch 361 and a STOP switch 362. The indicator array 304 includes an alarm indicator light 365, as well as a pressure gauge 366, an anticoagulant flow gauge 367 and a blood flow gauge 368. The pressure gauge 366 registers the so-called "trans-membrane pressure", i.e., the pressure at the inlet of the fractionator 25, as detected by a sensor coupled to the pressure fitting 356.

Figure 25A:
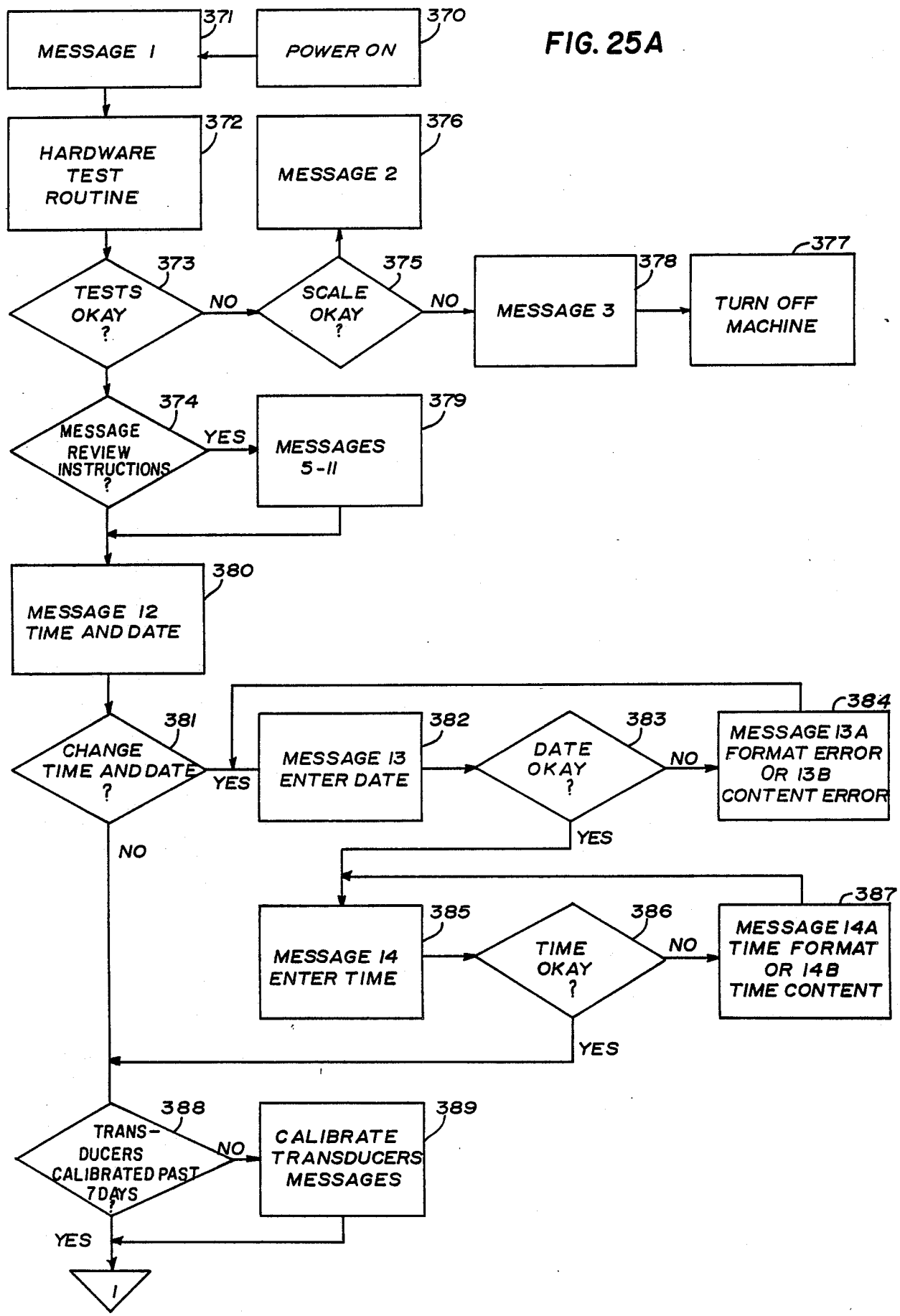
FIGS. 25A-25C are a flow diagram of the computer program for the system of FIG. 20.
Figure 25B:
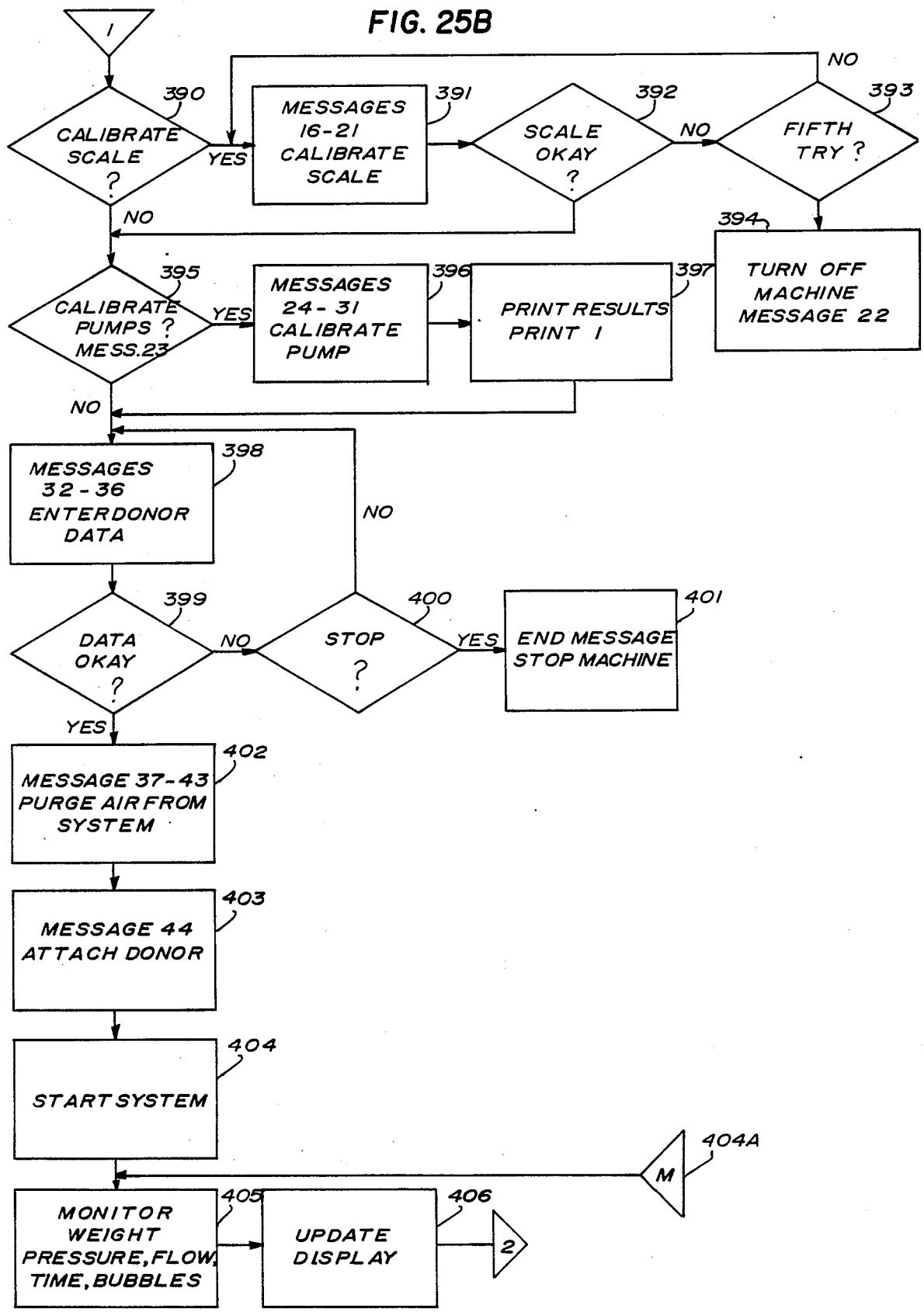
Figure 25C:
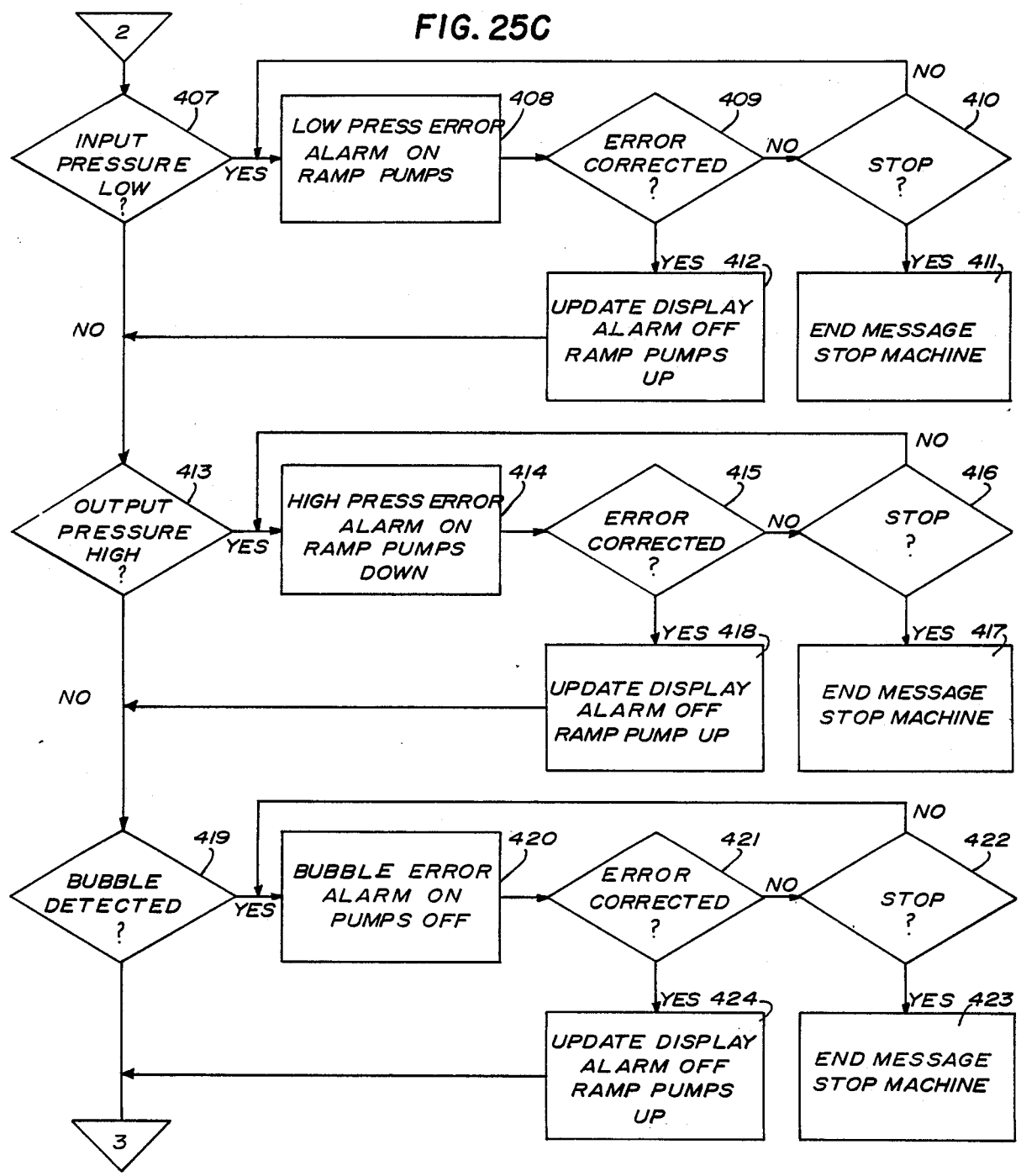
Figure 25D:
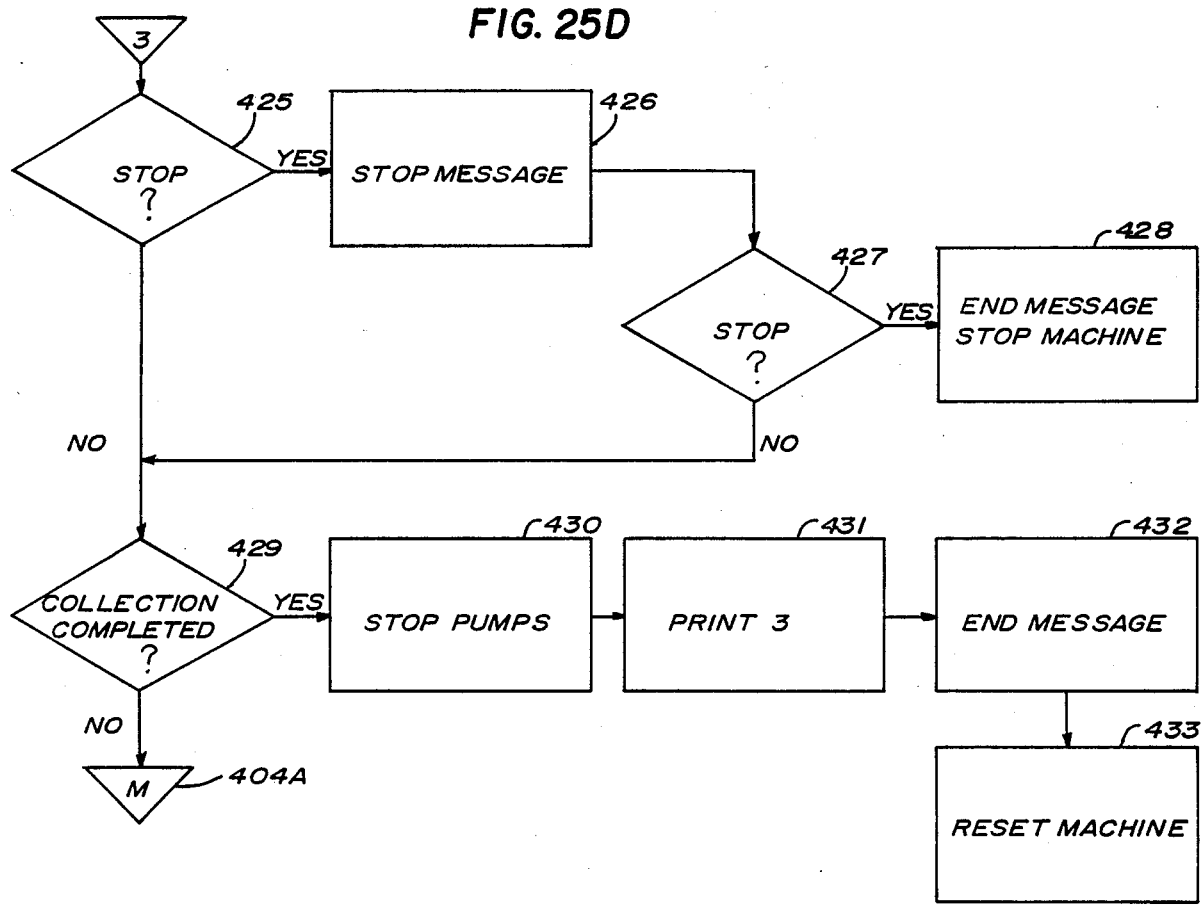

It will be appreciated that the microprocessor 301 operates under stored program control, the operation of the program being illustrated in the flow diagram of FIGS. 25A–25C. The program is menu-driven, with the menu messages appearing on the display screen 303. The various display messages which appear during the operation of the program, the possible user replies and the response of the system 300 to these replies are all set forth in Table V at the end of the specification. Referring now to the flow diagram of FIGS. 25A–25C and the messages of Table V, the operation of the system 300 will be described.

First of all, the power button 353 is pressed to power up the system, indicated at block 370 in the flow diagram. At this point, message 1 appears on the screen, as indicated in block 371, the text of the message appearing in Table V. In Table V, the message number of label is indicated above the text of the message. At block 372, the system then conducts a number of electronic hardware tests, and at decision 372 asks if all the tests have been passed successfully. If they have, the program drops to decision 374, and displays message 4. If all tests are not satisfactory, the fault must be in the scale or in one of the transducers. Thus, the program moves to block 375 and displays message 2 or 3 according to the nature of the fault, as indicated by blocks 376 and 378. After a predetermined delay, the program moves to block 377 and shuts down the machine rendering it inoperable.

Message 4 in decision 374 asks the user if he wants to review the system instructions. If an instruction review is requested, the program moves to block 379 and displays messages 5–11, then moving to block 380. It will be appreciated that in the case of multiple sequential messages, the messages do not appear on the screen simultaneously, but rather are sequentially actuated by user operation of a key on the key pad 302, as is standard procedure in the menu-driven systems. The particular buttons actuated by the user are set forth in Table V. If no review is requested, the program moves directly from decision 374 to block 380 and displays message 12 which displays the date and time and asks if the user wants to change them. The user response is evaluated at decision 381. If a change is requested, the program moves to block 382 to display enter date message 13. After the user enters the date the program moves to decision 383. Format and content of the entry are evaluated. If an error exists, the program moves to block 384 where one of two error messages are displayed. Control then returns to block 382. If no error exists the program moves to block 385 to display enter time message 14, whereupon a time entry is made by the user. At decision 386 format and content are evaluated. If an error exists the program moves to block 387 where one of two errors are dispayed. It then returns to block 385. If no error exists, the program moves to decision 388. If transducers have not been calibrated within one week's time, the program moves to a transducer calibration routine in block 389. "Transducer-Cal" message and "Cal"-messages 1–4 (see end of Table V) guide the user through the routine. The program then resumes at decision 390, where the user is asked if the scale is to be calibrated. If a calibration is requested, the program moves to block 391 to display messages 16–21 which instruct the user in scale calibration. At this point, the user follows the directions in the messages 16–21 and performs the scale calibration.

First, the user makes certain that the receptacle 340 is not touching the top wall 334 of the lower housing 331, and all items are removed from the receptacle 340. A 2 Kg. weight may be provided with the system as a weight reference standard. When the calibration procedure is followed, the measured weight should agree with the standard weight within +/−2 gram. At decision 392, the program asks if the scale is within tolerance. If it is, it proceeds to decision 395. If it is not, the program then asks at decision 393 if this is the fifth calibration attempt. If it is not, the program returns to block 391 for a retry. If this is the fifth calibration attempt, the program moves from decision 393 to block 394, displaying exit message 22. The machine is shut down and rendered inoperable.

After successful calibration of the scale, message 23 at decision 395 asks if the user wishes to calibrate the pumps. If no pump calibration is requested, the program proceeds to block 398. If pump calibration is requested, the program moves to block 397 and displays messages 24–31, which lead the user through the pump calibration procedure. In this regard, calibration kits may be provided with the system for use in calibration of the citrate pump 306 and the blood pump 308. At the end of calibration the calibration results are printed by printer 350.

At block 398, the program displays messages 32–36, which direct the user in entry and validation of donor data, including a donor ID number, donor weight in pounds, donor hematocrit in percent and donor sex. If either the weight or hematocrit values are beyond acceptable ranges, the program displays appropriate messages indicating that the donor is unacceptable and, at decision 400, displays the "Reset" message to ask the user if the system should stop. If the answer is yes, it moves to block 401, displays "End Message" and stops the machine. If no, the program returns to block 398.

If the data is acceptable, the program proceeds to block 402 and displays messages 37–43 which direct the user in the procedure for purging air from the system. At this point, the user will place the disposable fractionator unit 310 in place in the system 300, in the configuration illustrated in FIGS. 20 and 22. The plasma bag 325 (and 326, if necessary) is clamped in the receptacle 340 in the manner explained above. The fractionator 325 is mounted in the holder 335, the tube 318 is placed in the blood pump 308 and the tube 314 is placed in the citrate pump 306, and the spike 315 is inserted in the citrate bag 307. The bubble detector 323A is placed in an associated holder (not shown) on the lower housing 331, and the couplers 317 and 321 of the pressure lines 316 and 320, are respectively coupled to the Luer connectors 355 and 356. The citrate bag 307 is then unclamped, and the system operates the citrate pump 306 to drive citrate to purge air from the tubes 312 and 314. The blood pump then operates at a flow rate less than that of the citrate pump to purge air from the remainder of the system, the plasma bag 325 being clamped during this procedure. The bubble detector 323A will cause an alarm to sound until all the air has been purged. Message 42 instructs the user to press STOP when all air is purged.

Next, the program moves to block 403 and displays message 44, directing the user to connect the system to the donor. More specifically, the double-lumen needle 28 is inserted in the donor's vein and the clamps are removed from the plasma bag 325. The user then presses the START button, and the program moves to block 404 to initialize the system algorithm and move the program into a main loop, the return leg of which is designated at triangle 404A.

The system algorithm is set forth in Table VI at the end of the specification. The constants in step 1 are predetermined and placed in the system beforehand. In response to the start of the procedure at block 404, the initialization of the algorithm occurs at steps 2 and 3. The system also tares the scale weight to zero, turns on the pumps 306 and 308 and ramps them to a final speed over a time period of about five seconds at stop 4. The program then moves to blocks 405 and 406, repeatedly performing the measurements and calculations set forth at steps of the algorithm, updating these values each time the program cycles through the main loop, and displaying the values in "Run"-message (Table V) which is updated approximately every two seconds.

The main loop consists of FIG. 25C and triangle 404A and blocks 405 and 406 of FIG. 25B. During each traverse of this loop, the program moves to decision 407 to determine if the input pressure to the blood pump 308, as sensed via the tube 316, is within specifications. If it is, the program proceeds directly to decision 413, to check the output pressure ff the pump 308, i.e., the trans-membrane pressure of the fractionator 25, as sensed via the pressure line 320. If the input pressure is not correct, the program proceeds to block 408, sends an alarm, displays "Low-Press-Error" message, and ramps down the pumps 306 and 308. If the input pressurefalls below preset limits and pump speed has not changed, there must have been an increase of input resistance. The usual cause is inadequate blood flow from the vein. This, in turn, may be caused by a kinked tubing, a poorly placed needle, or a blood clot in the input line. The display asks the user to make certain checks and adjustments, and the program then moves to decision 409 to determine if the error has been corrected. If it has not, the user is asked if the program should stop at decision 410. If yes, it moves to block 411 and the machine is stopped. If no, the program resumes at 408 and continues to display the appropriate message. If the error is corrected, the program moves to block 412, clears the alarm and message and ramps up the pumps to resume the procedure.

In a similar manner, if the output pressure is incorrect, the program proceeds from decision 413 to block 414, sending an alarm and displaying "High-Press-Error" message and ramps down the pumps. The major component of flow resistance is the fractionator 25, and the blood pump output pressure approximates the trans-membrane pressure of the fractionator 25, which is displayed continuously on the pressure gauge 366. A rise in this pressure signifies increased resistance downstream from the blood pump. This may occur in the fractionator 25, the return tube 323, the bubble detector 323A or the tube 323B. A slight rise during the procedure is normal and represents gradual membrane pore size reduction by protein deposition. After the indicated checks have been made, the program moves to decision 415 and checks to see if the error has been corrected. If it is not, the user responds to decision 416 with yes or no. If yes, the program moves to block 417 where "End-Message" displays and the machine stops. If no, the program returns to block 414. If the error is corrected, the program moves to block 418 to clear the alarm and message and ramp up the pumps.

The program drops to decision 425 and asks if the STOP button 362 has been pressed. (Decision 419 and its branches are shown as part of the main loop but represent an interrupt, to be described later.) If it has, the program moves to block 426 and displays "Stop-Message" which asks the user if he really intended to stop. The program then moves to decision 427 and, if the user indicates that he does intend to stop, the program moves to block 428 to display "End-Message" and then stops the machine. If the user indicates that he does not intend to stop, the program resumes the main loop, proceeding to decision 429.

At decision 429 the program determines whether the desired weight of plasma has been collected. If it has, the program moves to block 430, stops the pumps and displays "End-Message" indicating that the plasma collection is complete. It then moves to block 431 and prints Print 3 (Table V). The program stops at blocks 432 and 433. If the desired amount of plasma has not yet been collected, the program returns to the start of the main loop, at triangle 404A.

If an air bubble has been detected, the program is interrupted immediately and moves to block 419 and stops the pumps 306 and 308, sounds an alarm and displays the "Bubble-Error" message at block 420 which directs the user to make certain checks, or to press the STOP button 362 to terminate the procedure. The program then moves to decision 421 to see if the error has been corrected. If it has, the program moves to block 424 to clear the alarm and message and ramp up the pumps, proceeding then to the point in the main loop at which the interrupt occurred. If the error has not been corrected, the program moves to decision 422. If the STOP button 362 has been pressed, the program moves to block 423, "End-Message" is displayed and the machine stops. If the STOP button is not pressed, the program returns to block 420 and continues the alarm message.

When the desired amount of plasma has been collected, the plasma bag 325 is clamped and severed from the remainder of the disposable fractionator unit 310, which then can be discarded. The system 300 is reset and a new collection procedure can then begin. It will be appreciated that if both bags 325 and 326 are used, when the bag 325 is filled, the plasma will flow automatically through the tube 329 into the bag 326. When the collection is completed, the system creates a printout of the data pertinent to that collection procedure. The data printed out is set forth in Print 3.

In a preferred embodiment of the invention, the system 300 is programmed to pump blood at 60 ml. per minute. Citrate-saline solution is pumped from the citrate bag 307 at a rate sufficient to dilute incoming plasma to 68% of the initial concentration. The total plasma collected is 18% of the calculated donor circulating plasma volume. Taking plasma volume at 5% of body weight, plasma collected will be 4.08 ml. per pound of body weight. If either pump 306 or 308 is slowed down by changes in pressure, both pumps slow proportionately and the ratio of the citrate to plasma flow remains constant. The system 300 operates so that the pumps 306 and 308 pump the preselected amount or they pump nothing. This prevents undetected slowing down of one pump relative to the other. Since the blood pump 308 pumps faster than the citrate pump 306, citrate always flows toward the fractionator 25, not toward the donor. The concentration of citrate is low enough that systemic citrate levels can never reach toxic concentrations. Since citrate is metabolized rapidly as a normal metabolite, systemic anticoagulation cannot occur as is the case with anticoagulants, such as heparin. The total volume of blood in the system 300 is less than 25 ml., so that a technical problem does not produce undue blood loss. When necessary, a new setup can be easily installed with minimal blood loos. The volume of citrate infused is less than the volume of plasma removed unless the filtration fraction falls below 0.3. Even if plasma were not filtered, the citrate infusion volume would not exceed 900 ml. per hour.

TABLE V

PLASMAPHERESIS CONSOLE MESSAGES

```
                  MESSAGE 1
***********************************************   Message displays on POWER ON.
*              WELCOME                        *   Machine performs internal checks
*     TO THE PLASMAPHERESIS SYSTEM             *   of components.
* PLEASE WAIT UNTIL THE SYSTEM IS TESTED *   If okay GOTO Message 4.
*        INSTRUCTIONS WILL FOLLOW.......*   If scale error GOTO Message 3.
***********************************************   If sensor error GOTO Message 2.

MESSAGE 2
***********************************************   Message displays.
*                                              *   Program terminates.
*TRANSDUCERS ARE NOT FUNCTIONING PROPERLY*
*                                              *
* PLEASE CHECK TROUBLE SHOOTING MANUAL...*
***********************************************

MESSAGE 3
***********************************************   Message displays.
*                                              *   Program terminates.
* THE SCALE IS NOT FUNCTIONING PROPERLY  *
*                                              *
* PLEASE CHECK TROUBLE SHOOTING MANUAL...*
***********************************************

MESSAGE 4
***********************************************   If YES pressed GOTO Message 5.
*     DIAGNOSTIC CHECKS WERE OKAY.       *   If NO pressed GOTO Message 12.
* DO YOU WISH TO REVIEW INSTRUCTIONS?  *
*                                              *
*       PRESS <<YES>> OR <<NO>>.....*
***********************************************

MESSAGE 5
***********************************************   If ENTER pressed GOTO Message 6.
*      THIS IS THE SETUP PERIOD          *   If REDO pressed GOTO Message 4.
*YOU MAY RECALL A PROCEDURE WITH <<REDO>>*
* YOU MAY ERASE AN ENTRY WITH <<CLEAR>>  *
*          PRESS <<ENTER>> TO CONTINUE.*
***********************************************

MESSAGE 6
***********************************************   If ENTER pressed GOTO Message 7.
* PRESSING << REDO >> WILL RETURN YOU    *   If REDO pressed GOTO Message 5.
*TO THE BEGINNING OF THE PREVIOUS DISPLAY*
*    YOU MAY TRY THIS NOW IF YOU WISH    *
*          PRESS <<ENTER>> TO CONTINUE.*
***********************************************

MESSAGE 7
***********************************************   If ENTER pressed GOTO Message 8.
* DURING SETUP YOU WILL BE ASKED TO DO   *   If REDO pressed GOTO Message 6.
*   VARIOUS TASKS. YOU MAY BE ASKED TO   *
* ENTER DATA OR TO PERFORM PROCEDURES.   *
*          PRESS <<ENTER>> TO CONTINUE.*
***********************************************

MESSAGE 8
***********************************************   If ENTER pressed GOTO Message 9.
* IF YOU MAKE A SETUP ERROR REMEMBER THAT*   If REDO pressed GOTO Message 7.
* <<STOP>> AND <<REDO>> ALLOW YOU TO MAKE*
* CORRECTIONS. USE <<CLEAR>> FOR TYPOS.  *
*          PRESS <<ENTER>> TO CONTINUE.*
***********************************************
```

```
                    MESSAGE 9
****************************************** If ENTER pressed GOTO Message 10.
* DURING SETUP AND DURING PLASMAPHERESIS  * If REDO pressed GOTO Message 8.
* YOU MAY BE ASKED TO REPLY TO QUESTIONS  *
*      BY PRESSING <<YES>> OR <<NO>>.     *
*           PRESS <<ENTER>> TO CONTINUE.  *
******************************************

MESSAGE 10
****************************************** If ENTER pressed GOTO Message 11.
*   PRESS NUMERIC KEYS TO ENTER DATA.     * If REDO pressed GOTO Message 9.
* PRESS <<ENTER>> TO COMPLETE THE ENTRY.  *
*    PRESS <<CLEAR>> TO ERASE AN ERROR.   *
*           PRESS <<ENTER>> TO CONTINUE.  *
******************************************

MESSAGE 11
****************************************** If ENTER pressed GOTO Message 12.
* IF YOU WISH TO REVIEW ANY INSTRUCTIONS, * If REDO pressed GOTO Message 10.
*   PRESS <<REDO>> UNTIL THE SCREEN YOU   *
*        WISH TO SEE IS DISPLAYED.        *
*           PRESS <<ENTER>> TO CONTINUE.  *
******************************************

MESSAGE 12
****************************************** Time and date are displayed.
*         THE DATE IS :   . .             * If YES pressed GOTO Message 13.
*         THE TIME IS :   .               * If NO pressed GOTO Message 15.
*         CHANGE TIME OR DATE?            * If REDO pressed GOTO Message 11.
*         PRESS <<YES>> OR <<NO>>.....    *
******************************************

MESSAGE 13
****************************************** User enters date.
*    ENTER THE DATE AS MM.DD.YY           * If a format error GOTO Format_error.
*    FOR EXAMPLE: 08.15.85                * If a content error GOTO Content_error.
*    PRESS <<ENTER>> IF NO CHANGE         * If data correct GOTO Message 14.
*    ENTER DATE :                         * If REDO pressed GOTO Message 12.
******************************************

FORMAT_ERROR  MESSAGE 13A
****************************************** If START pressed GOTO Message 13.
*      DATE FORMAT IS MM.DD.YY            * If REDO pressed GOTO Message 13.
*      USE ZERO IF NO NUMBER.             *
*      PLEASE REENTER DATE.               *
*         PRESS <<START>> WHEN READY....  *
******************************************

CONTENT_ERROR  MESSAGE 13B
****************************************** User's entry displayed.
*   THIS IS YOUR DATE ENTRY:              * If START pressed GOTO Message 13.
*   EITHER THE DAY OR MONTH IS WRONG.     * If REDO pressed GOTO Message 13.
* DATE FORMAT IS MM.DD.YY  PLEASE REENTER *
*         PRESS <<START>> WHEN READY....  *
******************************************

MESSAGE 14
****************************************** If ENTER pressed GOTO Message 15.
*       ENTER THE TIME AS HH.MM           * If REDO pressed GOTO Message 13.
*   (INTERNATIONAL TIME) EXAMPLE: 14.15   * If a format error GOTO Time_format
*       PRESS <<ENTER>> IF NO CHANGE      * If a content error GOTO Time_content.
*       ENTER TIME :                      * If data correct GOTO Message 15.
******************************************
```

```
               TIME_FORMAT    MESSAGE 14A
**********************************************  If START or REDO pressed GOTO Message 14
*        TIME FORMAT IS HH.MM                 *
*        USE ZERO IF NO NUMBER.               *
*        PLEASE REENTER TIME.                 *
*           PRESS <<START>> WHEN READY....    *
**********************************************

TIME_CONTENT   MESSAGE 14B
**********************************************
*   THIS IS YOUR TIME ENTRY:                  *  Data is displayed.
*   EITHER THE HOUR OR MINUTE IS WRONG.       *  If START or REDO pressed GOTO Message 14.
*   TIME FORMAT IS HH.MM  PLEASE REENTER      *
*           PRESS <<START>> WHEN READY....    *
**********************************************
*** Before Message 15 is displayed check date of last transducer calibration**
*** If more than one week GOTO Transducer_cal ***

MESSAGE 15
**********************************************  If NO pressed GOTO Message 23.
*      SCALE SHOULD BE CALIBRATED             *  If REDO pressed GOTO Message 13.
*      AT THE BEGINNING OF EACH DAY.          *  If YES pressed GOTO Message 16.
*      DO YOU WISH TO CALIBRATE SCALE?        *
*           PRESS <<YES>> OR <<NO>>.....      *
**********************************************

MESSAGE 16
**********************************************  User follows instructions.
*      REMOVE ALL OBJECTS FROM SCALE          *  If START pressed GOTO Message 17.
*         INCLUDING BAG HOLDER CLAMP          *  If REDO pressed GOTO Message 15.
*                                             *  If START pressed scale placed in
*           PRESS <<START>> WHEN READY..      *  calibration mode.
**********************************************

MESSAGE 17
**********************************************  User places calibration weight on
*                                             *  scale. REDO not permitted. Only
*   PLACE 2 KG WEIGHT IN CENTER OF SCALE.     *  START recognized.
*                                             *  When START pressed calibration
*           PRESS <<START>> WHEN READY..      *  is completed and GOTO Message 18.
**********************************************

MESSAGE 18
**********************************************  User follows instructions.
*                                             *  If REDO pressed GOTO Message 16.
*      REMOVE 2 KG WEIGHT FROM SCALE.         *  If START pressed scale is tared
*                                             *  and GOTO Message 19.
*           PRESS <<START>> WHEN READY..      *
**********************************************

MESSAGE 19
**********************************************  User follows instructions.
*                                             *  If REDO pressed GOTO Message 16.
*        PLEASE VERIFY CALIBRATION.           *  When START pressed scale takes a
*   PLACE 2 KG WEIGHT IN CENTER OF SCALE.     *  reading and compares it to 2 kg.
*           PRESS <<START>> WHEN READY...     *  GOTO Message 20 if reading is within
**********************************************  2 grams. GOTO Message 21 if error.

MESSAGE 20
**********************************************  If START pressed GOTO Message 23.
* THE MEASURED WEIGHT IS:         GRAMS.      *  If REDO pressed GOTO Message 16.
* DIFFERENCE FROM 2 KG IS:        GRAMS.      *
*   THE SCALE IS WITHIN TOLERANCE.            *
*           PRESS <<START>> WHEN READY...     *
**********************************************
```

MESSAGE 21

```
****************************************
* THE MEASURED WEIGHT IS:      GRAMS.  *
* DIFFERENCE FROM 2 KG IS:     GRAMS.  *
* OUT OF TOLERANCE - PLEASE RECALIBRATE *
*        PRESS <<START>> WHEN READY... *
****************************************
```
If START or REDO pressed GOTO Message 16.
If this message is read 5 times GOTO Message 22.

MESSAGE 22

```
****************************************
*  SCALE MALFUNCTION. PLEASE TURN OFF  *
*     THE MACHINE AND REFER TO THE     *
*  TROUBLESHOOTING GUIDE IN THE MANUAL.*
*                                      *
****************************************
```
User informed of failure after 5 trials. Program terminates. Program cannot be rerun without scale calibration.

MESSAGE 23

```
****************************************
*      PUMPS SHOULD BE CALIBRATED      *
*      AT THE BEGINNING OF EACH DAY.   *
*      DO YOU WISH TO CALIBRATE THEM?  *
*          PRESS <<YES>> OR <<NO>>..... *
****************************************
```
If YES pressed GOTO Message 24.
If NO pressed GOTO Message 32.
If REDO pressed GOTO Message 16.

MESSAGE 24

```
****************************************
* PLACE CALIBRATION KIT TUBING IN PUMPS.*
* NOTE THAT THE TUBES DIFFER IN SIZE.  *
* ASSURE THAT TUBING-PUMP PAIRS MATCH. *
*       PRESS <<ENTER>> TO CONTINUE.. *
****************************************
```
User follows instructions.
If ENTER pressed GOTO Message 25.
If REDO pressed GOTO Message 23.

MESSAGE 25

```
****************************************
*   ADJUST PUMPS FOR PROPER OCCLUSION  *
*   REMOVE BAG HOLDER CLAMP FROM SCALE *
*PLACE EMPTY CONTAINER IN CENTER OF SCALE*
*       PRESS <<ENTER>> TO CONTINUE... *
****************************************
```
User follows instructions.
If ENTER pressed GOTO Message 26.
If REDO pressed GOTO Message 24.

MESSAGE 26

```
****************************************
*   PLACE ENDS OF TUBES IN CONTAINER.  *
* TUBES MUST NOT MOVE DURING CALIBRATION*
*                                      *
*       PRESS <<START>> WHEN READY.... *
****************************************
```
User follows instructions.
If START pressed GOTO Message 27.
If REDO pressed GOTO Message 25.

MESSAGE 27

```
****************************************
* CITRATE PUMP CALIBRATION IN PROGRESS *
*       NO OF GRAMS   :                *
*       NO OF SECONDS :                *
*       PRESS <<STOP>> TO HALT PROCESS.*
****************************************
```
Scale is tared, reading is taken, time is marked and citrate pump runs at fixed rpm. Display is updated every 5 seconds.
If STOP pressed GOTO Message 29.
At end of 60 seconds pump stopped and GOTO Message 28.

MESSAGE 28

```
****************************************
*  BLOOD PUMP CALIBRATION IN PROGRESS  *
*       NO OF GRAMS   :                *
*       NO OF SECONDS :                *
*       PRESS <<STOP>> TO HALT PROCESS.*
****************************************
```
Citrate ml/rev calculated, scale is tared, time is marked and blood pump runs at fixed rpm. Display updated every 5 seconds.
If STOP pressed GOTO Message 30.
At end of 60 seconds pump stopped and GOTO Message 31.

```
               MESSAGE 29
***********************************************  Citrate pump stopped.
*    CITRATE PUMP CALIBRATION STOPPED !       *  If REDO pressed GOTO Message 23.
*                                             *  If START pressed GOTO Message 27.
*       PRESS <<REDO>> TO RESTART SETUP       *
*          PRESS <<START>> TO CONTINUE.....   *
***********************************************

MESSAGE 30
***********************************************  Blood pump stopped.
*    BLOOD PUMP CALIBRATION STOPPED !         *  If REDO pressed GOTO Message 23.
*                                             *  If START pressed GOTO Message 28.
*       PRESS <<REDO>> TO RESTART SETUP       *
*          PRESS <<START>> TO CONTINUE.....   *
***********************************************

MESSAGE 31
***********************************************  When REDO or ENTER pressed GOTO
*       BOTH PUMPS ARE CALIBRATED.            *  Print 1.
*                                             *  After Print 1 if REDO was pressed
*       PRESS <<REDO>> TO RESTART SETUP       *  GOTO Message 26. If ENTER was
*          PRESS <<ENTER>> TO CONTINUE.....   *  pressed GOTO Message 32.
***********************************************

PRINT 1
==================     This message printed on 16 column printer
!CITRATE PUMP=   !     at end of Message 31.
!        ML/REV  !
!BLOOD PUMP=     !
!        ML/REV  !
==================

MESSAGE 32
***********************************************  User enters donor I.D. number
*                                             *  and presses ENTER.
*    ENTER THE DONOR ID NUMBER:               *  When ENTER pressed GOTO Message 33.
*                                             *
*                                             *
***********************************************

MESSAGE 33
***********************************************  User enters <1> or <2> and presses
*                                             *  ENTER.
* ENTER DONOR SEX (1=FEMALE; 2=MALE):          *  When ENTER pressed GOTO Message 34.
*                                             *
*                                             *
***********************************************

MESSAGE 34
***********************************************  User enters donor's hematocrit value.
*                                             *  When ENTER pressed check value for
* ENTER DONOR HEMATOCRIT (PER CENT):           *   lower limits of male and and female.
*                                             *  If less than 38 and female GOTO Crit_error_female.
*                                             *  If less than 41 and male GOTO Crit_error_male.
***********************************************  If value okay GOTO Message 35.

CRIT_ERROR_MALE
***********************************************  Display value entered.
*    HEMATOCRIT ENTERED IS      PER CENT      *  If YES pressed GOTO Donor_end.
*    THE VALUE IS TOO LOW FOR A MALE           *  If NO pressed GOTO Message 34.
*    IS THIS HEMATOCRIT CORRECT?:              *
*          PRESS <<YES>> OR <<NO>>.....        *
***********************************************
```

```
              CRIT_ERROR_FEMALE
****************************************** Display value entered.
*  HEMATOCRIT ENTERED IS    PER CENT  * If YES pressed GOTO Donor_end.
*  THE VALUE IS TOO LOW FOR A FEMALE  * If NO pressed GOTO Message 34.
*     IS THIS HEMATOCRIT CORRECT?:    *
*         PRESS <<YES>> OR <<NO>>.....*
***************************************

MESSAGE 35
****************************************** User enters donor weight and
*                                       *   presses ENTER.
*  ENTER DONOR WEIGHT IN LBS:           * Value checked for upper and lower
*                                       *   acceptable limits. If out of range
*                                       *   GOTO Low_weight_error or High_weight_error.
****************************************** If value okay GOTO Message 36.

LOW_WEIGHT_ERROR
****************************************** Display value entered.
*  DONOR WEIGHT ENTERED IS    POUNDS.  * If YES pressed GOTO Donor_end.
*  THE WEIGHT IS LESS THAN 110 POUNDS! * If NO pressed GOTO Message 35.
*     IS THIS WEIGHT CORRECT?:         *
*         PRESS <<YES>> OR <<NO>>.....*
***************************************

HIGH_WEIGHT_ERROR
****************************************** Display value entered.
*  DONOR WEIGHT ENTERED IS    POUNDS.  * If YES pressed GOTO Donor_end.
*  THE WEIGHT IS MORE THAN 300 POUNDS! * If NO pressed GOTO Message 35.
*     IS THIS WEIGHT CORRECT?:         *
*         PRESS <<YES>> OR <<NO>>.....*
***************************************

DONOR_END
****************************************** After display of message program
*                                       *   terminates.
*   SORRY. THIS DONOR IS UNACCEPTABLE.  * If RESET pressed GOTO Reset.
*  PRESS <<RESET>> TO RESET THE MACHINE..*
*                                       *
***************************************

RESET
****************************************** If YES pressed GOTO End_message.
*  RESET WILL CANCEL THIS PROCEDURE    * If NO pressed GOTO Message 32.
*   AND WILL START A NEW PROCEDURE.    *
*       ALL DATA WILL BE ERASED.       *
*  DO YOU WISH TO RESET? <<YES>> OR <<NO>>*
***************************************

MESSAGE 36
****************************************** Display values entered.
*  THESE ARE THE VALUES ENTERED :      * If YES pressed GOTO Message 34.
*     WEIGHT :     POUNDS              * If NO pressed GOTO Message 37.
*     HEMATOCRIT :   PER CENT          *
*     CHANGE VALUES?  <<YES>> OR <<NO>>*
***************************************

MESSAGE 37
****************************************** User follows instructions and
*  THE NEXT STEPS WILL PURGE AIR FROM THE *   presses ENTER.
*    LINES AND FROM THE PLASMA_SEPARATOR. * If REDO pressed GOTO Message 36.
*  PLACE BAG OF CITRATE SOLUTION ON HOLDER* If ENTER pressed GOTO Message 38.
*         PRESS <<ENTER>> TO CONTINUE...*
***************************************
```

MESSAGE 38

```
************************************************
*        PLACE TUBING IN PUMPS.                *
*      PLACE PLASMA BAG IN SCALE.              *
*   PLACE PLASMA SEPARATOR IN HOLDER.          *
*          PRESS <<ENTER>> TO CONTINUE...      *
************************************************
```
User follows instructions and presses ENTER.
If REDO pressed GOTO Message 37.
If ENTER pressed GOTO Message 39.

MESSAGE 39

```
************************************************
*CLAMP CITRATE LINE AND INSERT BAG SPIKE.      *
*ATTACH PRESSURE LINES TO LUER CONNECTORS      *
*    PLACE NEEDLE IN WASTE RECEIVER.           *
*          PRESS <<ENTER>> TO CONTINUE...      *
************************************************
```
User follows instructions.
If REDO pressed GOTO Message 38.
If ENTER pressed GOTO Message 40.

MESSAGE 40

```
************************************************
*          OPEN CITRATE LINE.                  *
*    CLAMP PLASMA LINE NEAR PLASMA BAG.        *
*   PUMPS WILL PUMP CITRATE THROUGH SYSTEM.    *
*          PRESS <<ENTER>> TO CONTINUE...      *
************************************************
```
User follows instructions.
If REDO pressed GOTO Message 39.
If ENTER pressed GOTO Message 41.

MESSAGE 41

```
************************************************
*OBSERVE LINES FOR PURGING OF AIR BUBBLES      *
*   ASSIST AIR REMOVAL BY GENTLE TAPPING       *
*   <<START>> AND <<STOP>> CONTROL PUMPS.      *
*          PRESS <<START>> WHEN READY....      *
************************************************
```
If REDO pressed GOTO Message 40.
If START pressed, citrate pump is turned on and slowly increases speed to maximum. Blood pump turns on and slowly increases to speed less than citrate pump. When both pumps are full speed GOTO Message 42.

MESSAGE 42

```
************************************************
*                                              *
*  WHEN ALL AIR IS PURGED PRESS <<STOP>>...    *
*                                              *
*                                              *
************************************************
```
When STOP pressed both pumps stopped and GOTO Message 43.

MESSAGE 43

```
************************************************
*                                              *
*      PLEASE WAIT FOR A FEW MOMENTS           *
*                                              *
*                                              *
************************************************
```
Message displayed. Internal calculations are made, scale is tared, transducers are zeroed, time is marked, and variables are initialized.
When internal calculations finished GOTO Message 44.

MESSAGE 44

```
************************************************
*    INSERT NEEDLE INTO DONOR'S VEIN.          *
*     REMOVE CLAMP FROM PLASMA LINE.           *
*    WHEN BLOOD EXITS THE SEPARATOR.           *
*          PRESS <<START>> WHEN READY....      *
************************************************
```
If REDO pressed GOTO Message 37.
User places needle in donor vein.
When START pressed GOTO Print 2.
Printer started and then GOTO Run_message.

PRINT 2

```
===================
!BEGIN PROCEDURE  !
!TIME :           !
!DATE :           !
!DONOR            !
!DONOR WEIGHT:    !
!      POUNDS     !
```

This message prints out while system is running.

```
!FEMALE (MALE)    !
!HEMATOCRIT       !
!BLOOD FLOW IS    !
!        ML/MIN   !
!CITRATE FLOW IS  !
!        ML/MIN   !
!DILUTE PLASMA    !
!TO BE COLLECTED  !
!  IS        ML   !
!PLASMA VOLUME    !
!TO BE COLLECTED  !
!  IS        ML   !
===================
```

```
                                     If STOP pressed during procedure GOTO Stop_message
            RUN_MESSAGE
********************************************   This display is updated every few
*   TOTAL TIME ELAPSED        =    MIN      *   seconds. If pressure errors or
*   DILUTE PLASMA COLLECTED   =    ML       *   air bubble detected GOTO the
*   DONOR  PLASMA COLLECTED   =    ML       *   appropriate Message.
*   TOTAL CITRATE RETURNED    =    ML       *   Weights are taken continuously.
********************************************   When desired plasma amount obtained
                                                GOTO End_message and Print 3.
            HIGH_PRESS_ERROR
********************************************   If output pressure exceeds upper
*      DEVICE PRESSURE TOO HIGH         *   limit display message and decrease
*CHECK FOR OCCLUDED OR KINKED RETURN LINE*      pump speeds until pressure okay.
*  CHECK SEPARATOR AND BUBBLE DETECTOR.     *   Alarm flashes. When error corrected
*      PRESS <<START>> WHEN CORRECTED....*      press START. GOTO Run_message.
********************************************

LOW_PRESS_ERROR
********************************************   If input pressure is below limits
****CITRATE PUMP INPUT PRESSURE TOO LOW***      display message and decrease pump
* CHECK FOR OCCLUDED OR KINKED INPUT LINE*      speeds until pressure okay. Alarm
*       CHECK NEEDLE FOR OCCLUSION.         *   flashes. When error corrected GOTO
*       PRESS <<START>> WHEN CORRECTED....* Run_message.
********************************************

BUBBLE_ERROR
********************************************   Pumps stopped and message displayed
*      AIR DETECTED IN return LINE      *   any time a bubble is detected.
*  CHECK CONNECTIONS BEFORE CITRATE PUMP    * If START pressed return to place
*  AND AFTER SEPARATOR. PRESS <<START>      *   program was stopped. If STOP
*  WHEN CORRECTED OR <<STOP>> TO QUIT       *   pressed GOTO Stop_message.
********************************************

STOP_MESSAGE
********************************************   If YES pressed GOTO End_message.
*    PROCEDURE STOPPED BY OPERATOR !!       *   If NO pressed return to point of stoppage.
*                                           *
*    DO YOU WISH TO STOP THE PROCESS?       *
*         PRESS <<YES>> OR <<NO>>.....*
********************************************

END_MESSAGE
********************************************   If stop occurred during plasmapheresis
*      PROCEDURE HAS BEEN STOPPED.          *   GOTO Print_end and then terminate program.
*      ALL DATA HAS BEEN ERASED.            *   If stop occurred during setup terminate
*THE CONSOLE IS READY FOR A NEW PROCEDURE*      program.
*         PRESS <<START>> WHEN READY..*
********************************************
```

PRINT_END        Message printed at end of plasmapheresis.

```
==================
!PROCEDURE ENDED !
!TOTAL TIME:     !
!        MINUTES !
!TOTAL RUNTIME:  !
!        MINUTES !
!TIME :          !
!DATE :          !
!DONOR           !
!DONOR WEIGHT:   !
!        POUNDS  !
!FEMALE (MALE)   !
!HEMATOCRIT      !
!VOL.COLLECTED:  !
!PLASMA=     ML  !
!OIL.PL=     ML  !
!CITRATE RETURN= !
!        ML      !
==================
```

TRANSDUCER_CAL

```
*********************************************  Display message.
* PRESSURE TRANSDUCERS MUST BE CALIBRATED*     When ENTER pressed GOTO Cal_message 1.
* LAST CALIBRATION WAS MORE THAN 1 WK AGO*
* PLEASE CALIBRATE OUTPUT PRESSURE FIRST *
*         PRESS <<ENTER>> TO CONTINUE..  *
*********************************************
```

CAL_MESSAGE 1

```
*********************************************  User follows instructions.
*                                        *     When START pressed GOTO Cal_message 2
*                                        *
* REMOVE ANY CONNECTIONS TO OUTPUT PRESS *
*        PRESS <<START>> WHEN READY...   *
*********************************************
```

CAL_MESSAGE 2

```
*********************************************  User follows instructions.
* ATTACH GAGE LINE TO OUTPUT CONNECTOR   *     Message displays 150, 300, and 450
*                                        *     mm Hg in succession.
* ADJUST GAUGE TO READ ABOUT       MMHG  *     User enters gage reading.
* ENTER EXACT READING ON GAGE:           *     System calculates regression of
*********************************************  transducer output vs pressure.
                                               After last entry GOTO Cal_message 3
```

CAL_MESSAGE 3

```
*********************************************  User follows instructions.
*                                        *     When START pressed GOTO Cal_message 4
*                                        *
* REMOVE ANY CONNECTIONS TO INPUT PRESS  *
*        PRESS <<START>> WHEN READY...   *
*********************************************
```

CAL_MESSAGE 4

```
*********************************************  User follows instructions.
* ATTACH GAGE LINE TO INPUT CONNECTOR    *     Message displays -150, -300, and -450
*                                        *     mm HG in succession.
* ADJUST GAUGE TO READ ABOUT       MMHG  *     User enters gage reading.
* ENTER EXACT READING ON GAGE:           *     System calculates regression as above.
*********************************************  When calculations finished GOTO
                                               Message 15.
```

```
CAL_MESSAGE 5
*********************************************
*                                           * This message is displayed between each
*    PLEASE WAIT FOR A FEW MOMENTS          * gage entry for Cal_message 2 and 4.
*                                           *
*                                           *
*********************************************
```

TABLE VI

System Algorithm:

1. Place constants in system:

a. HCTD                 (donor hematocrit, decimal fraction)

b. BW                   (donor weight, pounds)

c. PDF=0.68             (plasma dilution factor)

d. CF=0.4706            (conversion factor, ml citrate per ml plasma)

e. SGP=1.026            (specific gravity plasma)

f. SGC=1.0024           (specific gravity citrate)

g. SGDP=1.0184          (specific gravity dilute plasma)

h. QB=60                (blood flow, ml/min)

i. RSG=1/SGDP j. C1=4.0824            (ml plasma collected/pound body weight)

k. C2=6.0035            (ml dilute plasma collected/pound body weight)

l. C3=1.9211            (ml citrate to be filtered/pound body weight)

m. CMR                  (citrate pump, ml per rev)

n. BMR                  (blood pump, ml per rev)

2. Calculate:

a. QP=QB*(1-HCTD)       (plasma flow, ml/min)

b. QC=QP*CF             (citrate flow, ml/min)

c. QBP=QB+QC            (blood pump, ml/min)

d. QCP=QC               (citrate pump, ml/min)

e. BRPM=QBP/BMR         (blood pump, rpm)

f. CRPM=QCP/CMR         (citrate pump, rpm)

g. MAXPF=BW*C1          (total plasma to collect, ml)

h. MAXDPF=BW*C2         (total dilute plasma to collect, ml)

i.  MAXCF=BW*C3               (total citrate to collect, ml j.  MAXDPW=MAXDPF*SGDP     (total dilute plasma to collect, gm)

3. Initialize sum variables to zero:

TDPW      (total dilute plasma filtered, gm)

TDPF      (total dilute plasma filtered, ml)

TPF       (total plasma filtered, ml)

TQB       (total blood flow, ml)

TQP       (total plasma flow, ml)

TQC       (total citrate flow, ml)

TRC       (total citrate returned to donor, ml)

TQ        (total flow, ml)

4. Ramp pumps to final rpm.

5. Main Loop:

A. Measure weight change per unit time for each pass through the loop.

B. Calculate:

TQB=TQB+($\Delta$t*(QBP-QCP)*0.0167)

TQP=TQB*(1-HCTD)

TQC=TQC+($\Delta$t*QCP*0.0167)

TQ=TQB+TQC

TDPW=total weight  (total dilute plasma filtered, gm)

DPFW=($\Delta$weight/$\Delta$time)*60  (dilute plasma filtered, gm/min)

DPF=DPFW*RSG      (dilute plasma filtered, ml/min)

TDPF=TDPW*RSG     (total dilute plasma filtered, ml)

PF=DPF*PDF        (plasma filtered, ml/min)

TPF=TDPF*PDF      (total plasma filtered, ml)

CF=PF*CF          (citrate filtered, ml/min)

TCF=TPF*CF        (total citrate filtered, ml/min)

TRC=TQC-TCF      (total citrate returned to donor, ml)

C. Compare TPF with MAXPF.
      If TPF less than MAXPF, repeat the loop.
      If equal or greater, stop the program.

While there has been described what at present in considered to be the preferred embodiment of the present invention, it will be understood that various modifications and alterations may be made therein without departing from the true scope and spirit of the present invention which is intended to be covered in the claims appended hereto.

I claim:

1. A method of collecting plasma from a living donor thereof, comprising: ascertaining the donor's initial plasma volume, extracting blood from the donor, and separating plasma from the extracted blood until a predetermined percentage of the donor's initial plasma volume has been separated.

2. The method of claim 1, wherein the plasma is separated from the donor's blood continuously until the predetermined percentage of the donor's initial plasma volume has been separated.

3. The method of claim 1, wherein the plasma is separated from the donor's blood in a series of batch operations until the predetermined percentage of the donor's initial plasma volume has been separated.

4. The method of claim 1, and further comprising returning to the donor the portion of the blood not separated.

5. A method of continuously collecting plasma from a human donor thereof, comprising: ascertaining the donor's initial plasma volume, passing at least a portion of the donor's blood through a device connected to the donor for continuously removing a portion of the plasma present in the blood until a predetermined portion of the donor's initial plasma volume has been removed from the donor.

6. The method of claim 5, wherein the device is serially connected to the donor and the blood flows between the donor and the device in a closed loop.

7. The method of claim 5, wherein the predetermined portion of plasma collected is a predetermined percentage and is substantially the same for each donor thereof.

8. The method of claim 7, wherein the predetermined portion is in the range of from about 16% by volume to about 20% by volume of the donor's initial plasma volume.

9. The method of claim 8, wherein the predetermined portion of the plasma collected from each donor is about 18% by volume.

10. The method of claim 5, and further comprising sensing the amount of plasma removed from the donor until the predetermined portion of the initial plasma volume as been removed and thereafter stopping the removal of plasma in response to the amount of plasma collected.

11. The method of claim 10, wherein the plasma volume is sensed by continuously weighing the plasma separated from the donor.

12. A method of adding anticoagulant to a source of blood, comprising: determining the plasma concentration in the blood, and adding an anticoagulant to the blood in an amount equal to a predetermined percentage of the plasma concentration.

13. The method of claim 12, wherein the plasma concentration is automatically determined from the blood hematocrit value.

14. The method of claim 12, wherein the ratio of the anticoagulant volume to the plasma volume in the blood is substantially the same for each source of blood.

15. The method of claim 12, wherein the volume ratio of anticoagulant to plasma in the blood is maintained in the range of from about 0.40 to about 0.50.

16. The method of claim 12, wherein the volume ratio of anticoagulant to plasma is maintained at substantially 0.47.

17. The method of claim 12, wherein the source of blood is a batch of blood previously taken from a human donor.

18. The method of claim 12, wherein the source of blood is a human donor and the blood is circulating in a closed loop to and from the donor during the addition of anticoagulant to the blood.

19. The method of claim 18, and further comprising passing the blood through an extracorporeal device in the closed loop.

20. A method of collecting plasma from a human donor thereof, comprising: ascertaining the donor's initial plasma volume, introducing anticoagulant to the blood from which the plasma is to be collected in an amount which is a predetermined percentage of the plasma in the blood, separating plasma from the blood, and collecting the separated plasma until a predetermined portion of the initial plasma volume has been collected.

21. The method of claim 20, wherein plasma is separated from the blood continuously, and anticoagulant is introduced into the blood only so long as plasma is being separated from the blood.

22. The method of claim 21, wherein the anticoagulant flow is a function of plasma flow.

23. The method of claim 20, wherein the anticoagulant is introduced into the blood in a batch process.

24. The method of claim 20, wherein the anticoagulant is present in the range of from about 40% to about 50% by volume of the plasma volume in the blood.

25. The method of claim 20, wherein the ratio of anticoagulant volume to plasma volume is substantially 0.47.

26. The method of claim 20, wherein the ratio of anticoagulant to plasma is maintained substantially constant for each donor.

27. A system for collecting blood plasma from a living donor thereof, comprising means for ascertaining the initial volume of plasma in the donor, means for extracting blood from the donor, and means for separating a predetermined portion of the donor's initial plasma volume from the extracted blood.

28. The system of claim 27, wherein said ascertaining means includes processing means operating under stored program control.

29. The system of claim 27, and further comprising means for measuring the amount of plasma which has been separated, and means responsive to said measuring means for controlling the operation of said separating means.

30. The system of claim 27, wherein said means for separating plasma from the blood includes a device connected in a closed blood loop with the donor for continuously passing blood through the device while separating plasma from the blood.

31. The system of claim 30, wherein said means for separating plasma from the blood includes a blood pump serially connected to the device.

32. The system of claim 31, and further comprising means for introducing anticoagulant to the blood in an amount equal to a predetermined percentage of the plasma in the blood.

33. The system of claim 32, wherein said means for introducing anticoagulant includes an anticoagulant source, a pump for pumping anticoagulant from said anticoagulant source into the closed loop, and means for controlling operation of the blood pump and the anticoagulant pump to deactivate same when the predetermined portion of the donor's initial plasma volume has been separated from the donor's blood.

34. The system of claim 33, and further comprising means for maintaining the blood flow rate and the anticoagulant flow rate substantially constant.

35. The system of claim 33, and further comprising means for controlling the anticoagulant flow rate as a function of plasma flow rate.

36. The system of claim 31, and further comprising means for controlling the blood pump to deactivate same when the predetermined portion of the donor's initial plasma volume has been separated from the donor's blood.

37. The system of claim 30, wherein said device is disposable.

38. A system of continuously collecting blood plasma from a donor thereof, comprising processing means including means for ascertaining the initial volume of plasma in the donor based on donor specific data, conduit means defining a closed blood loop with the donor, said conduit means including separating means for continuously separating a portion of the plasma in the donor's blood flowing therethrough; pump means for circulating the blood from the donor through said separating means in the closed loop; means for introducing anticoagulant from a source thereof to said conduit means in an amount sufficient to maintain the anticoagulant concentration within a predetermined percentage range of the plasma concentration in the blood flowing into said separating means container, means coupled to said separating means for collecting plasma separated thereby; and measuring means coupled to said container means for determining the amount of plasma collected therein; said processing means including control means responsive to the amount of plasma collected fro deactivating said pump means and said anticoagulant introducing means when a predetermined percentage of the donor's plasma volume has been collected.

39. The system of claim 38, wherein the donor specific data includes body weight and hematocrit.

40. The system of claim 38, wherein said processing means includes microprocessor means operating under stored program control.

41. The system of claim 40, and further comprising sensing means for ascertaining the pressures at the inputs of said pump means and said separating means, said processing means including means responsive to said sensing means for controlling the operation of said pump means and said anticoagulant introducing means.

42. The system of claim 41, wherein said processing means includes means for maintaining the anticoagulant flow rate as a predetermined function of the plasma flow rate.

43. The system of claim 40, wherein said stored program is menu driven, and further comprising display means coupled to said processing means for displaying menu messages and replies thereto, and input means coupled to said processing means for communicating thereto user replies to the menu messages.

44. The system of claim 38, and further comprising input means coupled to said processing means for supplying the donor specific data thereto.

45. The system of claim 38, wherein sadi conduit means is disposable.

46. The system of claim 38, wherein the system has a total blood volume of less than 25 ml.

47. The system of claim 38, and further comprising means for automatically calibrating said pump means.

48. The system of claim 38, and further comprising means for automatically calibrating said measuring means.

* * * * *